US008071307B2

(12) United States Patent
Tanaka et al.

(10) Patent No.: US 8,071,307 B2
(45) Date of Patent: Dec. 6, 2011

(54) METHOD OF DETECTING RELATIVE RISK FOR THE ONSET OF ATOPIC DERMATITIS BY GENE SINGLE NUCLEOTIDE POLYMORPHISM ANALYSIS

(75) Inventors: Keiko Tanaka, Swansea (GB); Julian M. Hopkin, Swansea (GB)

(73) Assignee: Asubio Pharma Co., Ltd., Minato-ku (JP)

( * ) Notice: Subject to any disclaimer, the term of this patent is extended or adjusted under 35 U.S.C. 154(b) by 679 days.

(21) Appl. No.: 11/887,769

(22) PCT Filed: Apr. 3, 2006

(86) PCT No.: PCT/JP2006/307062
§ 371 (c)(1),
(2), (4) Date: Nov. 26, 2008

(87) PCT Pub. No.: WO2006/107031
PCT Pub. Date: Oct. 12, 2006

(65) Prior Publication Data
US 2009/0098107 A1   Apr. 16, 2009

(30) Foreign Application Priority Data

Apr. 4, 2005   (JP) ................................. 2005-108045

(51) Int. Cl.
*C12Q 1/68* (2006.01)
(52) U.S. Cl. ..................... 435/6.11; 435/6.12; 435/6.17; 435/6.18
(58) Field of Classification Search .................... None
See application file for complete search history.

(56) References Cited

U.S. PATENT DOCUMENTS 5,942,392 A   8/1999   Amouyel et al. ................. 435/6

FOREIGN PATENT DOCUMENTS

| EP | 1 192 950 | 4/2002 |
| WO | 95/24504 | 9/1995 |
| WO | 01/16178 | 3/2001 |
| WO | 2005/017505 | 2/2005 |

OTHER PUBLICATIONS

International Search Report issued in the International (PCT) Application of which the present application is the U.S. National Stage, PCT/JP2006/30762 (Apr. 25, 2006).
K. Tanaka et al., "Genetic Variants of the Receptors for Thromboxane A2 and IL-4 in Atopic Dermatitis", Biochemical and Biophysical Research Communications, vol. 292, No. 3, pp. 776-780, Apr. 5, 2002.
C. Sengler et al., "Interactions Between Genes and Environmental Factors in Asthma and Atopy: New Developments", Respiratory Research, vol. 3, No. 1, pp. 1-15, Oct. 31, 2001.
X. Q. Mao et al., "Association Between Genetic Variants of Mast-Cell Chymase and Eczema", Lancet., vol. 348, No. 9027, pp. 581-583, Aug. 31, 1996.
X. Q. Mao et al., "Association Between Variants of Mast Cell Chymase Gene and Serum IgE Levels in Eczema", Hum Hered., vol. 48, No. 1, pp. 38-41, 1998.
T. Shirakawa et al., "Association Between Atopy and Variants of the β Subunit of the High-Affinity Immunoglobulin E Receptor", Nature Genetics, vol. 7, No. 2, pp. 125-130, Jun. 1994.
T. Shirakawa et al., "Association Between Atopic Asthma and a Coding Variant of FcεRIβ in a Japanese Population", Human Molecular Genetics, vol. 5, No. 8, pp. 1129-1130, Aug. 1996.
J. J. Kim et al., "Chemokine RANTES Promoter Polymorphisms in Allergic Rhinitis", Laryngoscope, vol. 114, No. 4, Abstract, Apr. 2004.
Tsunemi et al., "Interleukin-13 Gene Polymorphism G4257A is Associated with Atopic Dermatitis in Japanese Patients", Journal of Dermatological Science, vol. 30, No. 2, pp. 100-107, Nov. 2002.
S. Hoffjan et al., "The Genetics of Atopic Dermatitis: Recent Findings and Future Options", J. Mol. Med., vol. 83, No. 9, pp. 682-692, Sep. 2005.
Supplementary European Search Report issued Aug. 24, 2009 in corresponding European application, EP 06 73 1010.
K. Tanaka et al., "Association between mast cell chymase genotype and atopic eczema: comparison between patients with atopic eczema alone and those with atopic eczema and atopic respiratory disease", Clinical and Experimental Allergy (1999), vol. 29, No. 6, pp. 800-803.
H. Cox et al, "Association of atopic dermatitis to the beta subunit of the high affinity immunoglobulin E receptor", British Journal of Dermatology (1998), vol. 138, pp. 182-187.
A. Fryer et al., "The -403 G→A promoter polymorphism in the RANTES gene is associated with atopy and asthma", Genes and Immunity (2000), vol. 1, No. 8, pp. 509-514.
X. Liu et al., "An *IL 13* coding region variant is associated with a high total serum IgE level and atopic dermatitis in the German Multicenter Atopy Study (MAS-90)", Journal of Allergy and Clinical Immunology (2000), vol. 106, No. 1, pp. 167-170.
R. Nickel et al., "Atopic Dermatitis Is Associated with a Functional Mutation in the Promoter of the C-C Chemokine RANTES", The Journal of Immunology (2000), vol. 164, No. 3, pp. 1612-1616.

*Primary Examiner* — James Martinell
(74) *Attorney, Agent, or Firm* — Wenderoth, Lind & Ponack, L.L.P.

(57) ABSTRACT

The present invention provides a method of discriminating a relative risk for the morbidity of atopic dermatitis of a test subject comprising: analyzing gene polymorphism of two or more of genes related to onset of atopic dermatitis using a sample isolated from a statistically significant number of normal persons and patients of atopic dermatitis to determine relative ratios (percentages (%)) related to the individual gene polymorphism of individual derived from the analysis; and calculating an odds ratio according to specified gene polymorphism from the relative ratio; and using, as a discrimination criterion, a combination of two or more of gene polymorphisms showing a synergetically higher odds ratio than odds ratios according to individual gene polymorphism. The method is useful for predicting susceptibility of an AD patient to chemicals based on genes and for selecting the diagnostic and/or therapeutic agent by eliminating harmful drug reactions from the analysis of principal factors related to onset and development of AD and interaction among these genes, and for determining a diagnostic method and therapeutic method using the detection method of morbidity risk.

9 Claims, 1 Drawing Sheet

Fig. 1 calculation method of relative risk for the morbidity

|  | onset group | normal group |
|---|---|---|
| with risk factor | a | b |
| no risk factor | c | d |

$$\text{relative risk} = [a/(a+b)] / [c/(c+d)] = \frac{a(c+d)}{c(a+b)}$$

[a/(a+b)] — morbidity of person having risk factor

[c/(c+d)] — morbidity of person having no risk factor

Fig. 2 calculation method of odds ratio

|  | onset group | normal group |
|---|---|---|
| with risk factor | a | b |
| no risk factor | c | d |

$$\text{odds ratio} = \{[a/(a+c)]/[c/(a+c)]\}/\{[b/(b+d)]/[d/(b+d)]\} = (a/c)/(b/d) = ad/bc$$

[a/(a+c)]/[c/(a+c)] — odds ratio in onset group

[b/(b+d)]/[d/(b+d)] — odds ratio in normal group

SEQUENCE LISTING

```
<160> NUMBER OF SEQ ID NOS: 15

<210> SEQ ID NO 1
<211> LENGTH: 8124
<212> TYPE: DNA
<213> ORGANISM: Homo sapiens
<220> FEATURE:
<223> OTHER INFORMATION: Human mast cell chymase
<220> FEATURE:
<221> NAME/KEY: misc_feature
<222> LOCATION: (6680)..(6680)
<223> OTHER INFORMATION: n stands for any base

<400> SEQUENCE: 1
tcccagttaa tacataatca atatgcaatt tattaataca tctctccatg tccactcccc      60
ctgtatcttg ccattcttga cctgcatttc catcctcctt accttcccta gaggccaact     120
cattttcttt gaaaaacctg gcatttccca gaaaaaaaag tgaagggctg ggagctgtcc     180
gttgtcctga tttgctccct ctgccttgc ttccaaatgt ggttggaaag aagcactatt     240
gaaaaatccc taaacgcacc cctgcagggt tggctctacc ctgtagccat ggacacatgc     300
tgttgatacc acctgcctca tgagtctcac ataatttgcc ctttcacact atctacccca     360
tcagccttac caaaaccata cctgcatcct gggcagcatc tgcccttcaa gagactaagg     420
aatctccttg caaccaagaa tgactagacc aatgagacac cctttaaggc cccagcacaa     480
tatagaaatc ccacaatatg gtaatcccag taaggagcta tcaagccatt gcaggaccat     540
ctagaataca actagagtat agttcctttc aatccaggaa ctatactcta acagcttggc     600
tcacaggaac cagaagtgaa gatgatgagg atcagggctg agcctgtgag caccagctcc     660
accactgaca ccaaccacag attaaacaag catcttgtgg acccctggga tggaaagaat     720
```

```
agttgttgcc ttatcaacct cccccacagc ccacacagaa aagataaaat catcatggct    780
acagtgttac agaagatgat gacccaagga gtaggcctgc ctgagtgaat gctgagagtg    840
ataatgggag cagtagcatc tcagagacta cagcagaaac catccacata aagagctttg    900
cccaaactta tgataaaggg caccctcaga gactctccct actttaatat tagcccattg    960
cagaaatggt gagtggaaag agaaatctta ggaagaaccc cttaaaaaag caaaatgctt   1020
tttaggtttg tgctgaagag cctggaaaag aaataaggac acacacgctg agaaatcttc   1080
ctcctgcccc aacactggga taatctccaa ggatctctcc atatctcatt ctcctggata   1140
cactgtccac tcagaaatat tgtgcagagt gcagtaattc aaaagtgagc tattgtgtta   1200
ggagtgaagg caagagtatc gtaaaataaa tcaaatttga aatgaattct cttaaattgc   1260
tttatagatg tttaatgtaa gccagcagct attaaacgat aaaccttaaa ttcgagaaaa   1320
acttggtcat tcagaaacta tagaaacagg caggacttat tgcgagggca aacacagagt   1380
gagctccagc ctgcttcagg aaaatctgcc agtgccatga aggatgtact ctgtctgctc   1440
cactgcacta ctgctcagta tgagcccatg ccatcagctg tccctgaccc acaggagttc   1500
tttagaagag actggtcaac aaaagtttct agggtgtttt atacctgcca actcgagggt   1560
taaaacaagt tgcatagaaa tgctcaatca agaaagacac agtcattact cagagaataa   1620
taaacagcct ggcagcacat gaatgaatag aaaaaagatg ttacatgcaa agcatgaaat   1680
aaccaaattc cataacagat gttaatctgt aatgtgttta ggagaattta gaggaagtat   1740
aagatttatt ctttcatcaa aaaaattata gccaatgagg atatatctat caattatcca   1800
tcaagtggtg atatggcagc acaaggtaaa acacaaagga ataaaaccaa cgtttattaa   1860
gaaccaatca tgtggcattt cacattgagc atcatattta attctgaaaa aaatccttgt   1920
actgtatcat tcttcatatt ttatggatgc agtaactaag gctgagaact ttaaaatttt   1980
tcctaagttc agacacatag ctaagtggca gaaccaagat tcaaactcac cccatctaac   2040
tgcagagcaa actgcatgcc ttaaatgtca aagtgaatac tagcacagtt aatacaatgt   2100
ttggaaactc agagaaggaa tgatccctct gcattatagt tactaaggaa tcattgccat   2160
tatttaaatg ccagtgcttc tacatcaggc ccaaattttc tgtcctacta actgtgaatc   2220
aagacttgat tcaacctcta cttgagtatc tgccgcaatg agaaatcact tacctccact   2280
aaccacacat ttattttata acaacagatt gttagtaagt cctttcttat acatactcaa   2340
cagctgcttc ccaagatgct gtaggattat gtctagagtc aaactagcca gaagcaatgt   2400
ccaaaataca ccataacact gtgcagcaaa ggtcctacta ccacttgttt ggcccaaaca   2460
ttctaggcag cactggatat ctgaatcatc aattatttcc acaaacactg accctctac   2520 cagtcaccct cactagaaga attaattcca catgataata gctccctcat gttactccct   2580
tctaagtcaa attgtacacc cctttatctg attaacagag tctaagtcac atgacctaaa   2640
tgcaagagaa ctgggaatgg acgtttgtgg attctacctt agtaaggcaa agttatcatt   2700
gggaattcct ctaatacagg aagggtgttc cagagacatt aaggagccat ataaatggaa   2760
aatgtccact acaatccatc acttggttgc cccacatcaa cattcattct tttgccacac   2820
ttaaagtttc caagaacaaa aattatccca ctgaacataa tctttactat cttttatata   2880
aaggaaaatt agacttgact cagcagaact gaaataaccc agctctaaca gttactgctt   2940
ttaacttcaa gtactgtgtc tctaggtgat acctgctcca acaatagttt ggtcacattt   3000
tcaatttgat attctctagt ctcccaactt gataactgta ccctaaacca taagttcac    3060 taccaacatg ctatatataa aataaccaaa ggggaagaa gaaagagaaa aaggaaatct   3120
```

```
cttaaaatac acaggtatac atatgacaaa gcaaagaagg aaatgtgagc agatagtgca   3180
gtcctcgttt ctgaaattgg tccctgact ggggctatac ctattccatt tcctcaccct   3240
cagccaggca ggtggagcaa aaacttaagt cttggtggat ctgaatcttg atgctgtgga   3300
gctgtcttac tagccccaga ctacctgcct ctcaatttct aattatatca gtgaaagcaa   3360
acagctttga tttgtttaag cctctgattt tttggtctaa ctgatgtaag accacaagga   3420
caagagttct ccagctccgg attctcttct gttctgttaa tggtgaaatg cccgagagaa   3480
gagttgccaa cttttggcaaa taaaaaatac aggattccag ttaaattcaa atttagataa   3540
acaacaattt tttagtatta gtgtgtccca ttcaatattt ggacatactt aactaaaaaa   3600
tgatttgttg ttcatctgaa atacaaattt aactgggcat tctgaatatt ctctggcaac   3660
ccccgagaga gtgaagaaag tggtacaagg acacttaaga agaccagatt tgaaaagaca   3720
ttacggatgt gtttaaatgt cttattctag agagagttag agctgtaggt agaacttggg   3780
aaattaagtt aaaagcagac acagagacct ggccaatata tactaaggag tggatcactc   3840
tggtcacaag cccaacctga gaccaagggc atagtgagat gatttgggaa aggcacttat   3900
acactactca tccccgtctt tgaactaaat gccttataaa tctccaagag aaatgacagt   3960
ccaccatgtg gactgctttc tgtaagtcca gggaaaataa aagctatgtg cttgaaaccc   4020
acttctgata ttataaggtg tgtgatcttt gtcatgttaa tgggtctgag tatcaattct   4080
acaattgtaa agtgacagta atggtgtgtc cccaggttgt tgtggaaagc ttgattctta   4140
atgcaacagg aggaaacccc agcctctctg gagcaaacac ccttctacat ctttacttcc   4200
cctgcacatt ggcaggactc tattcctcta tttctctcta gtgctagagc agaaagggac   4260
cttgatttga tatcaggaaa atctatttct gaaccataag ctatgatagc tgatttaaaa   4320
aattgactat catgacatga taatgatcat aatggtaata catattgata gggttgccgt   4380
gaaagtaata atatatctaa gagttgtgac aatatatgat acgcctagac tctcagaaaa   4440
tgctaattcc aatcccaatt gctctttgca taaagttctg tcctagggtc tgttcttttc   4500
ccacatctac cctccttgga tctctcttct gtcttttca tgtggttcag aggaggagag   4560
agatccaggt caatgttttt caaattacaa ggaattatca tttaaatggg gaagaagctc   4620
aagttttgac gtgtagtgga attggagtgg agtggagtgg aatggaaact aacaggaaga   4680
cactgcacat ggttaagata aagattgttt cctgaaacct ttaatttgtg cttacatact   4740
cacacataca tatgtgcatg cactgggact ctgcaatatg catttctgac tatgaaacat   4800
agccataaaa gtctttgcac tgaacgttca gtgggccttt cacaagctgc cctaattggg   4860
aaagaaaaac atggtccctc catttcctgc cccaactcc agaaaagtca ccatagttga   4920
gggtacatct gagaagccag cacttgggag ttcagggctc aagttccttt ctagaaaaac   4980
actgggtgat tctaggggaa cttccgatca gaaacagcca attcagagtg agagaagaaa   5040
acgtgaccat gcagttcctg tggttaccag ccttgcccct ctcttgcctt ctgggagtta   5100 taaacccaa gactgaaaag gaaaaccagc atttgctcag gcagcctctc tgggaagatg   5160
ctgcttcttc ctctccccct gctgctcttt ctcttgtgct ccagagctga agctggtgag   5220
tatcagggtt cttccctctg aaatctgcag tatcagctcc tgaaacaaag atgtttagtc   5280
tgaaatagct gactcctaaa cagggttcca agatctctct tcaagagtcc cacagaggaa   5340
atttccactt gggatgtgtg ccaccccacc cccaccccca cccactgcca ttctctacag   5400
cctaggacac cccaggaac aaggaatttc acctcaattg tagaaaagcc cagagcaagt   5460
ggaaggaaaa ggggtatccc caggaaaaca gacatgtcct cttaatcttc tgagcatcag   5520
```

```
ggctacccat tactttgtga ctttctcact ctgtgaccat gctcaagagc tatggagaaa    5580
tctaaaacag gaacctggac agtgggtcct acacagagac agaggagagt gggccagggc    5640
aaggtgggag tgggagaagt ctgagatgaa acatcagaa tggagcagag caagaatga     5700 gatttcacct gggaggttat gggtggggaa agatacgaaa tacaggagac aggagaggga    5760
agatgggcgg aacacaggt gagaatgaga ttccagggaa gcctagctca gctttaaccc     5820
aatttgtcca ttcattggag agagtatcta tggccgtgtt caaaccctgg ggtgctctgt    5880
tccaggggag atcatcgggg gcacagaatg caagccacat tcccgcccct acatggccta    5940
cctggaaatt gtaacttcca acggtccctc aaaattttgt ggtggtttcc ttataagacg    6000
gaactttgtg ctgacggctg ctcattgtgc aggaaggtga gacaacaggg tctatttatc    6060
tccaaatggg agatgaacaa ccagagtagc atccaggaat acacctgcac tggggactga    6120 agaggggtc ctgggtcttg tcaactttca ggagagggaa gactttgggc tgaaagactt     6180
tagtctgtgt ttgaatagtt ccttgagcct cagtcactga gctaagctcc cttcggagga    6240
aaaggaggtc ctgtccgaag gtccctcttg ttgcagtagc acccctcacc cctacccaac    6300
tcaagacaca cggctcactt ttcagggccc cacccagtct cagggccact tcctctatgg    6360
ccttttcaag aacactggct ctagttctca gggtcctgaa cccatcattt tatgggagca    6420
gagaacaggt ctacataaga cccccacttt cccgttttaa ctgatatctc ctgcttcagg    6480
ggctggccct catgcagggt tccctgaatt aggaagtgtg aaccctgtcc cctgagtcct    6540
ccctggcctg ttcagtcccc agcaattcca ggggtcgtag aaattgtgtc tgtttcctga    6600
gaaagctctt tcatgagtta agcctgagcc ctcaaatgcc acaagtggcc catgaaaagg    6660
gagatgggta gagtccggcn acccagtgac agagtttagt cctctttttct cagaatgagc    6720 tcacctcaga agaaacccca agccatcact gtcgcctcct tttccttcct tcttcctcac    6780
agcaggtcta taacagtcac ccttggagcc cataacataa cagaggaaga agacacatgg    6840
cagaagcttg aggttataaa gcaattccgt catccaaaat ataacacttc tactcttcac    6900
cacgatatca tgttactaaa ggtgacaaca cctctcttct ccctttccac ttcccattct    6960
cctaagcttc tccttcaggt cctcattgcc ctgaattttt cttaggactt ggctataaca    7020
tgaagctact cacctgtcc ctccctgatc acctccaact gtccagagcc catttcgagg     7080
actgacagtc cttcattccc ttcacagttg aaggagaaag ccagcctgac cctggctgtg    7140
gggacactcc ccttcccatc acaattcaac tttgtccac ctgggagaat gtgccgggtg     7200
gctggctggg gaagaacagg tgtgttgaag ccgggctcag acactctgca agaggtgaag    7260
ctgagactca tggatcccca ggcctgcagc cacttcagag actttgacca caatcttcag    7320
ctgtgtgtgg gcaatcccag gaagacaaaa tctgcattta aggtgatcct ccaactaggt    7380
ttcctctcca aaactcactg ttcagggacc tgaatgctct tagaaggaga tggggtcagc    7440
aggttgtcag tcaggtgaca gggtgagcat cacaggaatt gctgtcctcc cgtggtccaa    7500
gacagcctct gaccatccat tccagtctac tgcactgggg gcatgggtg actgtggaga     7560 atgtggatga cggtcccaag aaaggaagaa ggggcatcag aactagatgt ataagtgagg    7620
agctccacct cctgggtctg actttaggtc tcactgtgac tccaagctgg ctggcagaca    7680
ggagtggagg acttcccggg ctcacttcct tctctctctc ctcccctac agggagactc     7740 tgggggcccct cttctgtgtg ctggggtggc ccagggcatc gtatcctatg acggtcgga    7800 tgcaaagccc cctgctgtct tcacccgaat ctccccattac cggccctgga tcaaccagat     7860
cctgcaggca aattaatcct ggatcctgag ccagcctgaa gggaagctgg aactggacct    7920
```

-continued

```
tagcagcaaa gtgtgtgcaa ctcattctgg ttctaccctt ggttccctca gccacaaccc      7980
taagcctcca agaggtctcc tacaggtaac agaactttca ataaacttca gtgaagacac      8040
agcttctagt cgtgagtgtg tgtccctctc tgctgctctc ttctcctgca catgtgacct      8100
gattcccagc ccaagcacca agga                                            8124
```

```
<210> SEQ ID NO 2
<211> LENGTH: 11298
<212> TYPE: DNA
<213> ORGANISM: Homo sapiens
<220> FEATURE:
<223> OTHER INFORMATION: FceRIb
<220> FEATURE:
<221> NAME/KEY: CDS
<222> LOCATION: (456..509)
<223> OTHER INFORMATION: /gene="high affinity IgE receptor beta chain"
      /codon_start=1
      /product="high affinity IgE receptor beta chain"
      /number=1
<220> FEATURE:
<221> NAME/KEY: CDS
<222> LOCATION: (1379..1510)
<223> OTHER INFORMATION: /gene="high affinity IgE receptor beta chain"
      /codon_start=1
      /product="high affinity IgE receptor beta chain"
      /number=2
<220> FEATURE:
<221> NAME/KEY: CDS
<222> LOCATION: (2026..2160)
<223> OTHER INFORMATION: /gene="high affinity IgE receptor beta chain"
      /codon_start=1
      /product="high affinity IgE receptor beta chain"
      /number=3
<220> FEATURE:
<221> NAME/KEY: CDS
<222> LOCATION: (4475..4531)
<223> OTHER INFORMATION: /gene="high affinity IgE receptor beta chain"
      /codon_start=1
      /product="high affinity IgE receptor beta chain"
      /number=4
<220> FEATURE:
<221> NAME/KEY: CDS
<222> LOCATION: (5079..5237)
<223> OTHER INFORMATION: /gene="high affinity IgE receptor beta chain"
      /codon_start=1
      /product="high affinity IgE receptor beta chain"
      /number=5
<220> FEATURE:
<221> NAME/KEY: CDS
<222> LOCATION: (5640..5738)
<223> OTHER INFORMATION: /gene="high affinity IgE receptor beta chain"
      /codon_start=1
      /product="high affinity IgE receptor beta chain"
      /number=6
<220> FEATURE:
<221> NAME/KEY: CDS
<222> LOCATION: (7224..7322)
<223> OTHER INFORMATION: /gene="high affinity IgE receptor beta chain"
      /codon_start=1
      /product="high affinity IgE receptor beta chain"
      /number=7
<220> FEATURE:
<221> NAME/KEY: intron
<222> LOCATION: 510..1378
<223> OTHER INFORMATION: /gene="high affinity IgE receptor beta chain"
      /number=1
<220> FEATURE:
<221> NAME/KEY: exon
<222> LOCATION: 1379..1510
<223> OTHER INFORMATION: /gene="high affinity IgE receptor beta chain"
      /number=2
<220> FEATURE:
<221> NAME/KEY: intron
<222> LOCATION: 1511..2025
<223> OTHER INFORMATION: /gene="high affinity IgE receptor beta chain"
      /number=2
```

```
<220> FEATURE:
<221> NAME/KEY: exon
<222> LOCATION: 2026..2160
<223> OTHER INFORMATION: /gene="high affinity IgE receptor beta chain"
      /number=3
<220> FEATURE:
<221> NAME/KEY: intron
<222> LOCATION: 2161..4474
<223> OTHER INFORMATION: /gene="high affinity IgE receptor beta chain"
      /number=3
<220> FEATURE:
<221> NAME/KEY: exon
<222> LOCATION: 4475..4531
<223> OTHER INFORMATION: /gene="high affinity IgE receptor beta chain"
      /number=4
<220> FEATURE:
<221> NAME/KEY: intron
<222> LOCATION: 4532..5078
<223> OTHER INFORMATION: /gene="high affinity IgE receptor beta chain"
      /number=4
<220> FEATURE:
<221> NAME/KEY: exon
<222> LOCATION: 5079..5237
<223> OTHER INFORMATION: /gene="high affinity IgE receptor beta chain"
      /number=5
<220> FEATURE:
<221> NAME/KEY: intron
<222> LOCATION: 5238..5639
<223> OTHER INFORMATION: /gene="high affinity IgE receptor beta chain"
      /number=5
<220> FEATURE:
<221> NAME/KEY: exon
<222> LOCATION: 5640..5738
<223> OTHER INFORMATION: /gene="high affinity IgE receptor beta chain"
      /number=6
<220> FEATURE:
<221> NAME/KEY: intron
<222> LOCATION: 5739..7223
<223> OTHER INFORMATION: /gene="high affinity IgE receptor beta chain"
      /number=6
<220> FEATURE:
<221> NAME/KEY: exon
<222> LOCATION: 7224..10214
<223> OTHER INFORMATION: /gene="high affinity IgE receptor beta chain"
      /number=7
<220> FEATURE:
<221> NAME/KEY: misc_feature
<222> LOCATION: (2966..2966, 2994..2994, 3498..3498, 3568..3568,
      3621..3621, 3627..3627, 3532..3632, 3665..3655, 3684..3684,
      3686..3686,  3764..3764, 3772..3772, 3810..3810, 3847..3847,
      4293..4293)
<223> OTHER INFORMATION: n stands for any base

<400> SEQUENCE: 2
aagcttttca aaggtgcaat tggataactt ctgccatgag aaatggctga attgggacac      60
aagtggggac aattccagaa gaagggcaca tctctttctt ttctgcagtt ctttctcacc     120
ttctcaactc ctactaaaat gtctcatttt caggttctgt aaatcctgct agtctcaggc     180
aaaattatgc tccaggagtc tcaaattttc ttatttcata ttagtcttta tttagtagac     240
ttctcaattt ttctattcat cacaagtaaa agcctgttga tcttaatcag ccaagaaact     300
tatctgtctg gcaaatgact tatgtataaa gagaatcatc aatgtcatga ggtaacccat     360
ttcaactgcc tattcagagc atgcagtaag aggaaatcca ccaagtctca atataataat     420
attctttatt cctggacagc tcggttaatg aaaaa atg gac aca gaa agt aat        473
                                      Met Asp Thr Glu Ser Asn
                                        1               5 agg aga gca aat ctt gct ctc cca cag gag cct tcc aggtaggtac            519
Arg Arg Ala Asn Leu Ala Leu Pro Gln Glu Pro Ser
         10                  15 aaggtattat tttttctac cctcagtcac ttgtggcagg ggaagtcata gtcacggtgc      579
ttaggagatg aaactttatt gatttaggca tggatccatc tagtttaatt aatatattgg     639
```

```
gtatgaggaa gctacttgct gtactttcca tgtggttctc tctccctgga gaggaacatt      699
tttactcagc ttgcaaactg gaaatagatt ttctcacatt agaagctcat tttctgggta      759
tgagacagga gagttcatac tgtgtatgta gatctctggc ttctgggtct gacatgtgct      819
gagggacaca tatccttcac acatgctttt ataaatactt gataaagtaa cctgcttctt      879
gattggtctt tataatccat aagctgtggg atgcttctct gaagatgaaa atagtaatag      939
agtcccatct agctattcaa agccattcct tcattgtatt ctgtgcacat gaagttgggg      999
tttgttactg acaaaatata ttcagataca tttctatgtt aaaaggattg tgagatgcat     1059
aggtaaatgt gtttattttc agttttactt gtcaacatag atgaatgaga aagaacttga     1119
aagtaacact ggattaagaa taggaaaatt tggcatggat tttgctccat tttgtcccat     1179
ctaatcactt ggatagtgtt caggtgttct tggtcagtta cttggatgct ctgagcttta     1239
gtttcttggt gattacaatg aagatttgaa ttacaggatg gctttgaaaa aataaacaaa     1299
actccccttt ctgtctgtcg agaatgttgc acagggagtt acagaatgtt ctcatgactg     1359
aattgctttt aaatttcac agt gtg cct gca ttt gaa gtc ttg gaa ata tct     1411
                      Ser Val Pro Ala Phe Glu Val Leu Glu Ile Ser
                                   20                  25 ccc cag gaa gta tct tca ggc aga cta ttg aag tcg gcc tca tcc cca     1459
Pro Gln Glu Val Ser Ser Gly Arg Leu Leu Lys Ser Ala Ser Ser Pro
30              35                  40                  45 cca ctg cat aca tgg ctg aca gtt ttg aaa aaa gag cag gag ttc ctg     1507
Pro Leu His Thr Trp Leu Thr Val Leu Lys Lys Glu Gln Glu Phe Leu
            50                  55                  60 ggg gtgagtgagc ctcctccaac tttgactaga gtaagggttg ggtctagaaa           1560
Gly agaatattga gttgcatcaa ctgttttccc acttggattc atgagaggtg ttaggtcctt     1620
taaaaaacat ggtagataaa gagttgacac taactgggtc cttttgggaa gagccagaag    1680
catttcctca taaagacttt aaattgctag gacgagaatg gccaacagga gtgaaggatt    1740 cataactttta tctttactta gatgtaaaga acaattactg atgttcaaca tgactacata    1800
cataaaggcg catggagaaa agtattggcc ttccatgcat taggtagtgc ttgtatcaat    1860
tcttatagtg gctagggtat cctggaaaat cttacgtgtg gatcatttct caggacagtc    1920
taggacacta acgcagtttc tcatgttgg cttctattat aaaaaatga tacaatctcg      1980 ggaaaatttt tttgatttc atgaaattca tgtgttttc tatag gta aca caa att     2037
                                                Val Thr Gln Ile
                                                            65 ctg act gct atg ata tgc ctt tgt ttt gga aca gtt gtc tgc tct gta     2085
Leu Thr Ala Met Ile Cys Leu Cys Phe Gly Thr Val Val Cys Ser Val
            70                  75                  80 ctt gat att tca cac att gag gga gac att ttt tca tca ttt aaa gca     2133
Leu Asp Ile Ser His Ile Glu Gly Asp Ile Phe Ser Ser Phe Lys Ala
            85                  90                  95 ggt tat cca ttc tgg gga gcc ata ttt gtgagtatat atctataatt            2180
Gly Tyr Pro Phe Trp Gly Ala Ile Phe
100                 105 gtttctgaaa taacactgaa cataggtttt tctctttctc agatctaacc agttgtttat     2240
tcccagtatt aagatgatat ttataattct taattataaa tatatgtgag catatataac     2300
atagatatgc tcattaacaa caacaaaaga ttcttttac aattaacggt gggttaaaca     2360
tttagcccac agttttatcc catgagaaac ctgaatctaa tacaagttaa atgacttgcc     2420
taagggccac ttgactaata gtaattgaac ctaaactttc agaatccaac tccaggaaca     2480
```

```
tacttctagc actattcatc aataaagtta tatgataaat acatacaact ttatctgtca    2540
actaaaaata acaacagagg ctgggcatgg tggctcacac ccgtaatccc agcactttgg    2600
gaggctgagg caggtggatc acctgaggtc aggagtttga gaccagcctg accaacatgg    2660
tgaaacctca tctctactaa atataaaaaa ttagctgagt gtgatagtgc atacctgtaa    2720
tccagctact taagaggctg aggcaggagg cttgtttgaa cctggaaggc agaggttgca    2780
gtgagctgag attgtgccat tgcactccag cctgggcaat aagtgcgaac tctgtctcaa    2840
aataataata ataataatag aaaataaagt tgtcttcatg aaaaatgagg aaagagattg    2900
ctggggtgag aaacattaag atcaatgggc atatggtgac cttctatgcc ctagaaactc    2960
ttttanggta ttttctcctg gtatctcttt tacncatcgt tctatctgga aaaataggtg    3020
gatgagtgag ataataacgg tatatacttt ttaaaggtct aattgacata tataaattgc    3080
aagtatttca gatgtcaatt tgctaacctt gacacacata gacacacatg aaaacatcac    3140
cacattaata caatgtatgt atccatcatt ccaaaagctt ccctgtgtat ctttgtaact    3200
ctttcttcct ccctccactc cttgtcctct cgttcccaag aaaacattga tctgcttcct    3260
gtgaatataa attaacttac atttttttaga gctttatata agtatgttct ctttactgtt    3320
tgtcttcctt cgctgcacag ttatttttgag attcttcaag ttttttcttt atatcgatac    3380
ttcattcaca agaatatatt ttaattctag actatgtcac attgactttg tcgtctgcta    3440
aatccttagt gctcagatga cttgttcagg actctccttg aacctgtacc tctgttanat    3500
tgaaacttgt ctctactgtc ttttttatttc aaacacagct tattaggtgt ctctcaaccc    3560
atcaaacnca caatctgagt cttaaggaga ttgctttgaa tttgtgctat tgacttatat    3620
ntatatnaaa tntgtaaatg tttggtaaaa atatcatcat gtacnttttc ataattacgc    3680
tatntncaca tgatatatgt cagactctgg aaatatgcat gccacagaca cgtgtttctt    3740
gcctaaaggg gctgatggaa gacncacata cnaatagacg attgcagtag aatgagagtg    3800
gtggtctaan cagtacatgt cctgatgttg ctcggacagt tactacncca agagtacccc    3860
ctgcattgtc agggttagca tctcctggaa gcctcatgta aatgaagaat tcatgctcc    3920
atccaggacc taatgaataa gaatctgcat tttagcaaga ccctcatatg attcatatac    3980
acttttttt ttttttttta gatggagtct cactcttgtc gcccaggctg gagtgcaatg    4040
gcatgatctt ggctcactgc aacctctgcc tcccgggttc aagtgattct cctgtctcag    4100
cctcccctagt agctgggact acaggtgcat gccacagtgg ctggctaatt tttgtatttt    4160
tagtagagac agggttttcac cattttggtc aggctggtct tgaactcatg acctccggtg    4220
attccccgc ctcggcttcc caaagtgctg ggattacaga catgagccac cacacccgcc    4280
ttattcgtat acncatttaa ttctgagaag cactctatag aaaataagaa taagaaaata    4340
ttgggctcac aggtgacatt aataagtaac tttatcgagt accccaaatt ttacctatgt    4400
ttggaagatg gggttaaaag gacacattga aaacaagaac tcattgtggc ttttttttcc    4460
tcctttttga acag ttt tct att tct gga atg ttg tca att ata tct gaa    4510
              Phe Ser Ile Ser Gly Met Leu Ser Ile Ile Ser Glu
                      110                 115
agg aga aat gca aca tat ctg gtgagttgcc cgtttctgtc tttgtccatc         4561
Arg Arg Asn Ala Thr Tyr Leu
120             125
cttgaaaaga taagaagaac agagttttaa gagtcttaag ggaaacacat ctttgtctcc    4621
tatattactt gtgaatgtgg atatatgatt tgtttcaat ctattttgtg tcctaaggct     4681
ttttgcaaca gaagttggat atatcattag aaacataaat tgtaccattt aacatacatg    4741
```

-continued

```
aagtttatgt ttaccttgac gttcttctaa aaagtgtcct acaccggcat tgtccttgta      4801
ggcatattca catgatcaaa taaaataatt agttttcaat taaggagaat atttgaggaa      4861
agaccgtacg tgttcatgtg gttcctgaag gcagtccagt gagaaagtaa tatatgcttc      4921
attaaacaat gcggacattt tcagggtttc ccttttttaac caaaatttgg aagcaatgtg    4981
gaatttactg gatgcatcca gccctgaaat gaagataggt ttattgaatg tgccagcaag     5041
tgcaggccca ggtctgagtg ttcttcatta ttatcag gtg aga gga agc ctg gga     5096
                                         Val Arg Gly Ser Leu Gly
                                                     130 gca aac act gcc agc agc ata gct ggg gga acg gga att acc atc ctg      5144
Ala Asn Thr Ala Ser Ser Ile Ala Gly Gly Thr Gly Ile Thr Ile Leu
        135                 140                 145 atc atc aac ctg aag aag agc ttg gcc tat atc cac atc cac agt tgc      5192
Ile Ile Asn Leu Lys Lys Ser Leu Ala Tyr Ile His Ile His Ser Cys
150                 155                 160 cag aaa ttt ttt gag acc aag tgc ttt atg gct tcc ttt tcc act          5237
Gln Lys Phe Phe Glu Thr Lys Cys Phe Met Ala Ser Phe Ser Thr
        165                 170                 175 gtatgtattt ttttttgtgt gggaagacta agattctggg tcctaatgta agtaagaagc    5297
cctcttctcc tgttccatga acaccatcct tttctgtaac ttctattaca cagtatagtg    5357
gttctgtaag ttcacacagc ccagggagat gctggctgcc cactcccctc aacccaggca    5417
aattcctcgg ggttaaagtt atctactgca agtgacgatc tctgggtttt tctgtgcctg    5477
tgtttgtgtg tgtgtgtgtg tgtgtgtgtg tgtgtatgtg tcactttaaa aggactggtc    5537
agatggtagg gagatgaaaa caggagatgc tataagaaaa taaactttg gggcgaatac     5597 caatgtgact cttttttgttt gtcatttgtt gctgttcaat ag gaa att gta gtg     5651
                                               Glu Ile Val Val
                                                       180 atg atg ctg ttt ctc acc att ctg gga ctt ggt agt gct gtg tca ctc      5699
Met Met Leu Phe Leu Thr Ile Leu Gly Leu Gly Ser Ala Val Ser Leu
        185                 190                 195 aca atc tgt gga gct ggg gaa gaa ctc aaa gga aac aag gtagatagaa       5748
Thr Ile Cys Gly Ala Gly Glu Glu Leu Lys Gly Asn Lys
200                 205                 210 gcccgatata aaatcttgaa tgacaggtta acgaattgga gctttattcc ttaaaatatg    5808
gcctgggttt tctgaaacat ttcttccaga aaatagtttc tccaagtttt attactttgg   5868
tttacaaatc tcacattaa atcacatttt ataccataag tagcacacat ttcataatat     5928
tcctctgaat gagggttggg ataataggac tgatatgtta gaaatgcctt aaagtgtgtg    5988
gagcatgaga gatggatgta cagaaggctt gtgaggaaac cacccaggta tctggccttg   6048
ttttctgccc cagaactagc cgcctattcc tgttttctgtt ttattccttt gtttcttgac   6108
ttttcctttc caacttgctc taaaacctca gttttctttc ctttctgatt catgactacc    6168
aaatgttttc acttgcctca cccgtccatt acacctttga taagaaccac cagaccttgt   6228
gctcatgtac ttgcccatgt ctgatggaag aaacatactc tctccatctg tccactttcc   6288
tgaggcattc aagtctagcc accttttaaa atcactctcc tccaggctgg cacggtgtc    6348 acgcctgtaa tctcagcact ttgtgaggct gaggagggcg gatcacttga agtcaggagt    6408 tcaaaccag cctggccaaa tggcaaaacc aaatcttctt caattataac caaatcttaa     6468
accaaatctc tactaaaaaa tacaacaaaa caaacaacaa caacaaaaa cagaaaagga    6528 aacattagcc cagcgtggtg gcaggtacct gaggttccag atacttggga ggctgaagca    6588
ggagaatcgc ttgagcccaa gagatggagg ttgcagtgag ccgagatcat gccactgcac    6648
```

| | |
|---|---|
| cacagccagg gtgacagagc catacttccc agcacattgg gaggccaaag ctgaagaata | 6708 |
| atttgaggtg aggatttgga gaccagcctg gccaacatgg tgaaactccg tctgtactaa | 6768 |
| aaatataaaa cttagtgggg catggggca cacacctgta atttcagcta cttaggaggc | 6828 |
| tgaggcagga gaattgcttg aacccgggag gcggaagttg cagtgagcca agatcgtggc | 6888 |
| cactgcactc cagcctgggt gacatagtga gattctgtct caaaaaaat aaagaaatt | 6948 |
| taaaaaatca ctctcttcca agatagata aataagacag cagatatact aaggaataac | 7008 |
| ctcaccaact tgtcattgac tgacatgatt tcttttggcc cacttggcca gctagtctgg | 7068 |
| tttggttttc tggaaatgaa agaaataatc agagtttaat gacagagagc gtgagaccca | 7128 |
| gaaagacaaa agtagatgag gtaagtctct tgagcgagac ttctagggat gggaaatttg | 7188 |

```
tggtgattga tatgaaatga tttttccctt atcag gtt cca gag gat cgt gtt          7241
                                      Val Pro Glu Asp Arg Val
                                                       215 tat gaa gaa tta aac ata tat tca gct act tac agt gag ttg gaa gac          7289
Tyr Glu Glu Leu Asn Ile Tyr Ser Ala Thr Tyr Ser Glu Leu Glu Asp
    220                 225                 230 cca ggg gaa atg tct cct ccc att gat tta taa gaatcacgtg tccagaacac       7342
Pro Gly Glu Met Ser Pro Pro Ile Asp Leu
235                 240
```

| | |
|---|---|
| tctgattcac agccaaggat ccagaaggcc aaggttttgt taaggggcta ctggaaaaat | 7402 |
| ttctattctc tccacagcct gctggtttta cattagattt attcgcctga taagaatatt | 7462 |
| ttgtttctgc tgcttctgtc caccttaata tgctccttct atttgtagat atgatagact | 7522 |
| cctattttc ttgttttata ttatgaccac acacatctct gctggaaagt caacatgtag | 7582 |
| taagcaagat ttaactgttt gattataact gtgcaaatac agaaaaaaag aaggctggct | 7642 |
| gaaagttgag ttaaactttg acagtttgat aatatttggt tcttagggtt ttttttttt | 7702 |
| ttagcattct taatagttac agttgggcat gatttgtacc atccaccat acccacacag | 7762 |
| tcacagtcac acacacatat gtattactta cactatatat aacttcctat gcaaatattt | 7822 |
| taccaccagt caataataca ttttgccaa gacatgaagt tttataaaga tctgtataat | 7882 |
| tgcctgaatc accagcacat tcactgacat gatattattt gcagattgac aagtaggaag | 7942 |
| tggggaactt ttattaagtt actcgttgtc tggggaggta aataggttaa aaacagggaa | 8002 |
| attataagtg cagagattaa catttcacaa atgtttagtg aaacatttgt gaaaaagaa | 8062 |
| gactaaatta agacctgagc tgaaataaag tgacgtggaa atggaaataa tggttatatc | 8122 |
| taaaacatgt agaaaagag taactggtag attttgttaa caaattaaag aataaagtta | 8182 |
| gacaagcaac tggttgacta atacattaag cgtttgagtc taagatgaaa ggagaacact | 8242 |
| ggttatgttg atagaatgat aaaaagggtc gggcgcggag gctcacgcct gtaatcccag | 8302 |
| cccttggga ggccgaggtg ggcagatcac gaagtcagta gtttgagacc agcctggcca | 8362 |
| acatagtgaa accccgtctc tactaaaaat acaaaaaaaa aattagctgg gtgtggtggc | 8422 |
| agtcacctgt agtcccagct acttgggagg atgaggcagg agaatcgctt gaacctggga | 8482 |
| ggcggaggtt gcagtgagcc gagatcgcac cagtgcactc cagccttggt gacaatggga | 8542 |
| gactccatct caaaaaaaaa aaaaaaaaa aaaagataaa aagtcagaaa tctgaaaagt | 8602 |
| ggaggaagag tacaaataga cctaaattaa gtctcatttt ttggctttga ttttggggag | 8662 |
| acaaagggaa atgcagccat agagggcctg atgacatcca atacatgagt tctggtaaag | 8722 |
| ataaaatttg atacacggtt tggtgtcatt ataagagaaa tcattattaa atgaagcaag | 8782 |
| ttaacactct aagagaatta ttttgagata gaagtgaagc taagctaaac ttcacatgcc | 8842 |

```
tataattgga gggaaaaact aaggataaaa tctagcctag aagatacaat aattagtcat    8902
aaacatgcat tgtgaaactg tagagagcag gtagcccaaa atagagaaag attagataaa    8962
gagaaaataa gtatccatca gagacagtat ctctaggctt gggcaagaga aaagtccaca    9022
gtgataagca actccaccta aggcatgaat atgcggcaga gaaaacagca atagtgaatg    9082
aatgcaaaag gtgctgagca aattccacac atgagtattg tgcatgagta aatgaataaa    9142
acatttgcaa agacctttag agaaagagaa tgggagcata tgtgcgaaat aagatagttg    9202
attatgaata gaaggtagtg aagaaaagca agctaagaaa aaattctgtt tataaaagaa    9262
ggaaaagata gtttatgttt ttagcctaag tataagagtc ctacagatgg actgaaaaaa    9322
atcagtctga gagtattagt cacaattaat gaaataatta cattttatgt attgaggatg    9382
ccaagattaa aaggtgacag gtagatgtta atttccctag attgtgaaag tgatcacgac    9442
aatcacacaa caaataatta agtgacttgg tatgctttat ttaattgtag ggcctgaggt    9502
tttccattct cattttctta aaatacaatt ttgtttctcc aaatttgaca gcagaataaa    9562
aaccctaccc tttcactgtg tatcatgcta agctgcatct ctactcttga tcatctgtag    9622
gtattaatca catcacttcc atggcatgga tgttcacata cagactctta accctggttt    9682
accaggacct ctaggagtgg atccaatcta tatctttaca gttgtatagt atatgatatc    9742
tcttttattt cactcaattt atattttcat cattgactac atatttctta tacacaacac    9802
acaatttatg aattttttct caagatcatt ctgagagttg ccccacccta cctgcctttt    9862
atagtacgcc cacctcaggc agacacagag cacaatgctg gggttctctt cacactatca    9922
ctgccccaaa ttgtctttct aaatttcaac ttcaatgtca tcttctccat gaagaccact    9982
gaatgaacac cttttcatcc agccttaatt tcttgctcca taactactct atcccacgat    10042
gcagtattgt atcattaatt attagtgtgc ttgtgacctc cttatgtatt ctcaattacc    10102
tgtatttgtg caataaattg gaataatgta acttgatttc ttatctgtgt ttgtgttggc    10162
atgcaagatt taggtactta tcaagataat ggggaattaa ggcatcaata aaatgatgcc    10222
aaagaccaag agcagtttct gaagtcctcc ttttcatcag ctctttatca aacagaacac    10282
tctataaaca acccatagcc agaaaacagg atgtaggaac aatcaccagc acactctata    10342
aacaacccat agccagaaaa cagaatgtaa ggacaatcac cagccatctt ttgtcaataa    10402
ttgatggaat agagttgaaa ggaactggag catgagtcat atttgaccag tcagtcctca    10462
ctcttattta cttgctatgt aaacttgaga aagcttttt ctctttgtga acctcaggtt    10522
ttacatctga aaatgagaaa tttggaacaa aagattccta actggtcttt ctgttcccat    10582
attctgtgat ttttcaatat ttaggatttt tggtaatcac aattacttag tttgtggttg    10642
agatagcaac acgaatcaga actatttggt ggacatattt tcaaaggagt agctctccac    10702
tttgggtaaa gaagtgatgc aggtcgtggt ggctcacgcc tgtaatccca gcactttagg    10762
gaggccaagg cggtggatc acgaggtcag gagatcgaga ccatcctggc taacacggtg    10822
aaaccccgtc tctactaaaa aatacaaaaa attagccagg cgtggtggcg ggcgcctgta    10882
gtcccacgta ctcgggaggc tgaggcagga gaatggcatg aaccaggag gcggagcttg    10942
ccgtgagccg agatagcgcc actgcagtcc ctcctgggca aaagagcaag actgcgtctc    11002
aaaaaaaaaa aaaaaaaaaa aaaagaagt gtgtggagta gcaggacacc tgcaacaata    11062
atatttttct aaatccctct gaaaaatgct aatcaaaggg ttttttttcct aaaaattgtc    11122
ttagaaataa aatttcccct ttgggagacc gaggctggca gatcacgagg tcaggagata    11182
gagaccacgg tgaaaccccg tctctactaa aaatactaaa aattagccgg ggagtggtgg    11242
```

-continued

```
tgggtacacc tgtagtccca gctacttgga ggctgaggct ggagaatcac gtgaac        11298
```

<210> SEQ ID NO 3
<211> LENGTH: 1016
<212> TYPE: DNA
<213> ORGANISM: Homo sapiens
<220> FEATURE:
<223> OTHER INFORMATION: RANTES
<220> FEATURE:
<221> NAME/KEY: mRNA
<222> LOCATION: 959..1011
<220> FEATURE:
<221> NAME/KEY: CDS
<222> LOCATION: 1014..1016
<223> OTHER INFORMATION: /gene="RANTES pro-inflammatory cytokine"
    /note="Only start codon is shown"
    /codon_start=1

<400> SEQUENCE: 3

```
gtcgaggatc cctaaagtcc tttgaagctt tcatattctg taacttttgt gccaagaagg      60
ccttacagtg agatgggatc ccagtattta ttgagtttcc tcattcataa aatggggata    120
ataatagtaa atgagttgac acgcgctaag acagtggaat agtggctggc acagataagc    180
cctcggtaaa tggtagccaa taatgataga gtatgctgta agatatcttt ctctccctct    240
gcttctcaac aagtctctaa tcaattattc cactttataa acaaggaaat agaactcaaa    300
gacattaagc acttttccaa aggtcgctta gcaagtaaat gggagagacc ctatgaccag    360
gatgaaagca agaaattccc acaagaggac tcattccaac tcatatcttg tgaaaaggtt    420
cccaatgccc agctcagatc aactgcctca atttacagtg tgagtgtgct cacctccttt    480
ggggactgta tatccagagg accctcctca ataaacact ttataaataa catccttcca    540
tggatgaggg aaaggaggta agatctgtaa tgaataagca ggaactttga agactcagtg    600
actcagtgag taataaagac tcagtgactt ctgatcctgt cctaactgcc actccttgtt    660
gtcccaagaa agcggcttcc tgctctctga ggaggacccc ttccctggaa ggtaaaacta    720
aggatgtcag cagagaaatt tttccaccat tggtgcttgg tcaaagagga aactgatgag    780
ctcactctag atgagagagc agtgagggag agacagagac tcgaatttcc ggagctattt    840
cagttttctt ttccgttttg tgcaattcca cttatgatac cggccaatgc ttggttgcta    900
ttttggaaac tccccttagg ggatgcccct caactggccc tataaagggc cagcctgagc    960
tgcagaggat caagacagca cgtggacctc gcacagcctc tcccacaggt acc atg      1016
                                                                Met
                                                                 1
```

<210> SEQ ID NO 4
<211> LENGTH: 5670
<212> TYPE: DNA
<213> ORGANISM: Artificial Sequence
<220> FEATURE:
<223> OTHER INFORMATION: Synthetic Construct; Human interleukin-13
    precursor
<220> FEATURE:
<221> NAME/KEY: mRNA
<222> LOCATION: (2158..2345)
<223> OTHER INFORMATION: /gene="IL-13"
    /product="interleukin-13 precursor"
    /number=1
<220> FEATURE:
<221> NAME/KEY: mRNA
<222> LOCATION: (3403..3456)
<223> OTHER INFORMATION: /gene="IL-13"
    /product="interleukin-13 precursor"
    /number=2
<220> FEATURE:
<221> NAME/KEY: mRNA

```
<222> LOCATION: (3709..3813)
<223> OTHER INFORMATION: /gene="IL-13"
      /product="interleukin-13 precursor"
      /number=3
<220> FEATURE:
<221> NAME/KEY: mRNA
<222> LOCATION: (4160..5095)
<223> OTHER INFORMATION: /gene="IL-13"
      /product="interleukin-13 precursor"
      /number=4
<220> FEATURE:
<221> NAME/KEY: exon
<222> LOCATION: 2158..2345
<223> OTHER INFORMATION: /gene="IL-13"
<220> FEATURE:
<221> NAME/KEY: CDS
<222> LOCATION: (2214..2345)
<223> OTHER INFORMATION: /gene="IL-13"
      /codon_start=1
      /product="interleukin-13 precursor"
      /number=1
<220> FEATURE:
<221> NAME/KEY: CDS
<222> LOCATION: (3403..3456)
<223> OTHER INFORMATION: /gene="IL-13"
      /codon_start=1
      /product="interleukin-13 precursor"
      /number=2
<220> FEATURE:
<221> NAME/KEY: CDS
<222> LOCATION: (3709..3813)
<223> OTHER INFORMATION: /gene="IL-13"
      /codon_start=1
      /product="interleukin-13 precursor"
      /number=3
<220> FEATURE:
<221> NAME/KEY: CDS
<222> LOCATION: (4160..4267)
<223> OTHER INFORMATION: /gene="IL-13"
      /codon_start=1
      /product="interleukin-13 precursor"
      /number=4
<220> FEATURE:
<221> NAME/KEY: sig_peptide
<222> LOCATION: 2214..2273
<223> OTHER INFORMATION: /gene="IL-13"
<220> FEATURE:
<221> NAME/KEY: Mat_peptide
<222> LOCATION: join(2274..2345,3403..3456,3709..3813,4160..4264)
<223> OTHER INFORMATION: /gene="IL-13"
      /product="interleukin-13"
      /function="cytokine"
      /evidence=experimental
<220> FEATURE:
<221> NAME/KEY: intron
<222> LOCATION: 2346..3402
<223> OTHER INFORMATION: /gene="IL-13"
<220> FEATURE:
<221> NAME/KEY: exon
<222> LOCATION: 3403..3456
<223> OTHER INFORMATION: /gene="IL-13"
<220> FEATURE:
<221> NAME/KEY: intron
<222> LOCATION: 3457..3708
<223> OTHER INFORMATION: /gene="IL-13"
<220> FEATURE:
<221> NAME/KEY: exon
<222> LOCATION: 3709..3813
<223> OTHER INFORMATION: /gene="IL-13"
<220> FEATURE:
<221> NAME/KEY: intron
<222> LOCATION: 3814..4159
<223> OTHER INFORMATION: /gene="IL-13"
<220> FEATURE:
<221> NAME/KEY: exon
<222> LOCATION: 4160..5095
<223> OTHER INFORMATION: /gene="IL-13"
<220> FEATURE:
<221> NAME/KEY: repeat_region
<222> LOCATION: 4831..4878
```

```
<223> OTHER INFORMATION: /rpt_type=direct
<220> FEATURE:
<221> NAME/KEY: polyA_site
<222> LOCATION: 5076..5081
<223> OTHER INFORMATION: /gene="IL-13"
<220> FEATURE:
<221> NAME/KEY: repeat_region
<222> LOCATION: 5522..5567

<400> SEQUENCE: 4
```

| | | | | | |
|---|---|---|---|---|---|
| ggatccccgc | tgacaatcta | gaaacaagca | acagaccctc | tgatgtagcc | atctgtgccg | 60 |
| cgcctctccg | caccgcccgc | cacgcccttgg | tccctggaga | ccaccctcca | gggcaggggc | 120 |
| tgccgctcgg | ccgggcccgc | ggggtccctc | ggcctgacat | ggccggtgct | ggagcggcac | 180 |
| gtgcgcgcct | cggcccctcg | gccgctcccg | ccctcgccg | gtgcgcaccg | gcgctcgggg | 240 |
| agccgctggc | ccgggtgtcc | agccggccct | tgccctgcct | ggcgctcgga | ccgccacctt | 300 |
| tgccgccccc | tcgccagcct | ccgcagcttc | cagactggcc | ggtctgcgcg | cccaccctg | 360 |
| cctcccggac | cggccaccgc | cggaggccgc | ggaggagggc | ccggccgcgc | agatcccgct | 420 |
| tatcgggccc | catctcccgt | tacataaggc | cacccccccta | tctccgcggg | ccatcgccgc | 480 |
| cgcaaccgcc | gcgccagcgc | cttctcccac | gcgcgggggc | gcccctgccc | accgctcccg | 540 |
| gcagggcttt | tggtggccat | gggggataag | gggcgttgac | tcacccgggc | ggggctccgg | 600 |
| gagttgcaca | gaccaaggta | gttccccgct | ccttccccca | tcacggagac | cctgtgggag | 660 |
| atgccgtggg | ccctctacta | cagattagga | aacaggcccg | tagaggggtc | gcgcggccaa | 720 |
| gtagcggcac | tccaggcact | gggggccctc | gaggaagg | gcagacttct | gggagtcaga | 780 |
| gccagcagct | gggctgggaa | gcttcgagtg | tggacagaga | gggtgggaat | gacgttccct | 840 |
| gtgggaagag | agggtgggca | agcctgggat | gcctctgagc | gggaatccag | catgccttgt | 900 |
| gaggagggtc | acaagcacac | ccttgtgagg | aggttgagcc | ccatcgagga | caggacggag | 960 |
| ggagcctgag | caggcagaga | gggggcctgg | ggaggcgctg | gttcggggag | gaagtgggta | 1020 |
| ggggagaaat | cttgacatca | acacccaaca | ggcaaatgcc | gtggcctctg | ctgtggggt | 1080 |
| ttctggagga | cttctaggaa | aacgagggaa | gagcaggaaa | aggcgacatg | gctgtagggc | 1140 |
| caagcccagg | agccgccctc | cacagcactc | attctgcaga | agggaaattt | gaggccccca | 1200 |
| gacggcaggg | gttgatcctg | cagagactgg | tgagcaaagg | ggatcacccc | aagcccagt | 1260 |
| ggcactagga | acacttacaa | tctctgacct | ggactaaggc | tgccagcctg | gcccagttaa | 1320 |
| gagtttccca | gaaggatggc | ccatacactt | taaattaaag | gggccagaca | cgtgcacact | 1380 |
| acttccagcc | actctggaag | ctgaggtggg | gggatcgctt | gagtctggga | gttggaggcc | 1440 |
| agcctaggca | ggcaacatag | tgagacccca | tctccaaaaa | aacaaaacaa | aacaaaacaa | 1500 |
| aaaaacacca | aaaaagctcc | cagaaagacc | tctgaatctt | tctggatctc | tcagtggaga | 1560 |
| cctggaaatc | tgaactttga | caatccctct | cacagtgggg | ccaaggagga | attaggcaag | 1620 |
| ccaaaagaag | tgaactttac | tcttctattg | cctgtttgaa | ttttgtatcc | aagcaagtgt | 1680 |
| tacttaagta | atttaagaga | ctggttcatc | gaaaaaataa | aactccccaa | attcccatag | 1740 |
| ctggtagact | gtggtcacag | ccacagtgca | ctaagactat | ctgctcagca | cttctggtga | 1800 |
| cccaaaaggg | tctgaggaca | ggagctcaga | gttgggtcag | ctgtccaggt | actcagggtt | 1860 |
| gtcacaggca | aaactgctgg | aactcagggc | agcattgcaa | atgccacgcc | gctctcaggg | 1920 |
| ccccttgcct | gccgctggaa | ttaaaccccac | ccagatcttg | gaaactctgc | cctggaccct | 1980 |
| tctcaataag | tccatgagaa | atcaaactct | tccttatg | cgacactgga | ttttccacaa | 2040 |
| agtaaaatca | agatgagtaa | agatgtggtt | tctagatagt | gcctgaaaaa | gcagagacca | 2100 |

```
tggtgtcagg cgtcaccact tgggcctata aaagctgcca caagacgcca aggccacaag    2160
ccacccagcc tatgcatccg ctcctcaatc ctctcctgtt ggcactgggc ctc atg       2216
                                                           Met
                                                           1 gcg ctt ttg ttg acc acg gtc att gct ctc act tgc ctt ggc ggc ttt    2264
Ala Leu Leu Leu Thr Thr Val Ile Ala Leu Thr Cys Leu Gly Gly Phe
          5                  10                  15 gcc tcc cca ggc cct gtg cct ccc tct aca gcc ctc agg gag ctc att    2312
Ala Ser Pro Gly Pro Val Pro Pro Ser Thr Ala Leu Arg Glu Leu Ile
          20                  25                  30 gag gag ctg gtc aac atc acc cag aac cag aag gtgagtgtcg gctagccagg   2365
Glu Glu Leu Val Asn Ile Thr Gln Asn Gln Lys
          35                  40 gtcctagcta tgagggctcc agggtgggtg attcccaaga tgaggtcatg agcaggctgg   2425
gcctggtcct aagatgcctg taggtcagga aaaatctcca tggaccaagg cccggcccag   2485
ccatgaggga gagaggagct gggctggggg gctcagcact gtggatggac ctatggaggt   2545
gtctggcaga ctccccaggg actacctgct ctcctggcct ggccttgtct gccactgcca   2605
gctcctactc agccattcct gaacagagga cagcagagaa gggccagcac cctcccagaa   2665
ccatgtggca tttgccaact ggattttgac cataacaatg cagccattct ccccagcacc   2725
atcataggcc cgcccttaca ggaggattcg ttagtagagt ccgctccttg ccccactagt   2785
aacagctcac atgtctgagc actgcttaca ccaggcctgg tgcacgtgct ttatgtgtca   2845
tttcatcact gccagccacc tcaagaggca ggtacgatga acccattctg ctaaggttca   2905
gtgaggttaa gtgacagagg ctggattcaa gccaggcctg ccaacacca gagtgtccat    2965
gctcctaact gcagtgttcc ctcaccatca gaaggcaggg catttaatac accagatccc   3025
caccgcctcc catctgattt gtcttggtca acagtggccc aggccactcc tacttcactc   3085
gtccccaccc tggcccttcc cgcaggcccc tgtcctcctg ccctgactat ggcaagcctt   3145
gcatgcagct tgtcccttac tagtggtgtc aattttttc tctcagctcc aagaccctaa    3205
acagtgggac ctcacccccta tgcctgctgt tcaaagcaga aaacgaagct caggaatgct  3265
gaggggctgc caggcctgcc tctgtgccac accagggatg cttgtggggc ctgtgctggg   3325
gcagacctgg cctgggctgc cagggcaggc cacaaccccc tgccagcact ctgctcactg   3385
tcactttgct cccacag gct ccg ctc tgc aat ggc agc atg gta tgg agc      3435
                   Ala Pro Leu Cys Asn Gly Ser Met Val Trp Ser
                             45                  50                  55 atc aac ctg aca gct ggc atg gtaaggacct ttgggtgcag ggaggatggg        3486
Ile Asn Leu Thr Ala Gly Met
              60 gcagaggctc caggccttgg gcttatcttc tctgagcctc ccttccatgg ctggggttcc   3546
aagcaagctt caagtgctct cctccctccc gccataatct ggccccttcc cgcccaccac   3606
ccagactcac ctgcgccagg catctcagcc ccatcttcct gcagactcac aaaaggcagc   3666
tgcccaagca gggcctgacc cctcggtgtc cctcccccac ag tac tgt gca gcc     3720
                                                  Tyr Cys Ala Ala
                                                           65 ctg gaa tcc ctg atc aac gtg tca ggc tgc agt gcc atc gag aag acc    3768
Leu Glu Ser Leu Ile Asn Val Ser Gly Cys Ser Ala Ile Glu Lys Thr
          70                  75                  80 cag agg atg ctg agc gga ttc tgc ccg cac aag gtc tca gct ggg        3813
Gln Arg Met Leu Ser Gly Phe Cys Pro His Lys Val Ser Ala Gly
          85                  90                  95 gtaaggcatc ccccaccctc tcacacccac cctgcacccc ctcctgccaa ccctgggctc   3873
```

-continued

```
gctgaaggga agctggctga atatccatgg tgtgtgtcca cccagggGTG gggccattgt    3933
ggcagcaggg acgtggcctt cgggatttac aggatctggg ctcaagggct cctaactcct    3993
acctgggcct caatttccac atctgtacag tagaggtact aacagtaccc acctcatggg    4053
gacttccgtg aggactgaat gagacagtcc ctggaaagcc cctggtttgt gcgagtcgtc    4113
ccggcctctg gcgttctact cacgtgctga cctctttgtc ctgcag cag ttt tcc      4168
                                                 Gln Phe Ser
                                                         100 agc ttg cat gtc cga gac acc aaa atc gag gtg gcc cag ttt gta aag     4216
Ser Leu His Val Arg Asp Thr Lys Ile Glu Val Ala Gln Phe Val Lys
            105                 110                 115 gac ctg ctc tta cat tta aag aaa ctt ttt cgc gag gga cgg ttc aac     4264
Asp Leu Leu Leu His Leu Lys Lys Leu Phe Arg Glu Gly Arg Phe Asn
        120                 125                 130 tga aacttcgaaa gcatcattat ttgcagagac aggacctgac tattgaagtt          4317
gcagattcat ttttctttct gatgtcaaaa atgtcttggg taggcgggaa ggagggttag    4377
ggaggggtaa aattccttag cttagacctc agcctgtgct gcccgtcttc agcctagccg    4437
acctcagcct tcccttgcc cagggctcag cctggtgggc ctcctctgtc cagggccctg    4497
agctcggtgg acccagggat gacatgtccc tacacccctc ccctgccta gagcacactg    4557 tagcattaca gtgggtgccc cccttgccag acatgtggtg ggacagggac ccacttcaca    4617
cacaggcaac tgaggcagac agcagctcag gcacacttct tcttggtctt atttattatt    4677
gtgtgttatt taaatgagtg tgtttgtcac cgttggggat tggggaagac tgtggctgct    4737
ggcacttgga gccaagggtt cagagactca gggccccagc actaaagcag tggaccccag    4797
gagtccctgg taataagtac tgtgtacaga attctgctac ctcactgggg tcctggggcc    4857
tcggagcctc atccgaggca gggtcaggag aggggcagaa cagccgctcc tgtctgccag    4917
ccagcagcca gctctcagcc aacgagtaat ttattgtttt tcctcgtatt taaatattaa    4977
atatgttagc aaagagttaa tatatagaag ggtaccttga acactggggg aggggacatt    5037
gaacaagttg tttcattgac tatcaaactg aagccagaaa taaagttggt gacagatagg    5097
cctgattgta tttgtctttc attttggcct ttggggacac tggtctgtgg tctgaagact    5157
ctgaggagct cttcgggagg ctggtgggtt ggaggagggg actgggatgg attacagcga    5217
gggtagggtg cagtgacctg ggctgaatgc aagctagctc ccgagggtgg ggacatggcc    5277
tgaaggaagc cccaccttct gtctgctgca ccagcaagga cggagaggct tgggccagac    5337
tgtcagggtt caaggagggc atcaggagca gacggagacc caggaagtct cacaatcaca    5397
tctcctgagg actggccagc tgtgtctggc accaccaca catccatgtc ccctcacaa     5457 cccaggaggc cgatgagaac tgtgaggctc agaaagcgtg ggcggtttgc ctaaggtcac    5517
gtagctactt cctcactggg gtcctgggc ctcagcct catctgaggt aaaggagcaa      5577
agttgggatt ggggtccaaa attcacttta actccaaagc ccacacactt aaccaccctg    5637
cctatttctg tccaaatgtc acctgtcctg aat                                 5670
```

<210> SEQ ID NO 5
<211> LENGTH: 132
<212> TYPE: PRT
<213> ORGANISM: Artificial Sequence
<220> FEATURE:
<223> OTHER INFORMATION: Synthetic Construct; Human interleukin-13
      precursor

<400> SEQUENCE: 5

```
Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
            35                  40                  45

Asn Gly Ser Met Val Trp Ser Ile Asn Leu Thr Ala Gly Met Tyr Cys
50                      55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130
```

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct; Primer

<400> SEQUENCE: 6
cagagtctaa gtcacatgac c          21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct; Primer

<400> SEQUENCE: 7
tgaccagagt gatccactcc            20

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct; Primer

<400> SEQUENCE: 8
cagaatgttc tcatgactga attg        24

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct; Primer

<400> SEQUENCE: 9
caagtacaga gcagacaact g           21

<210> SEQ ID NO 10
<211> LENGTH: 18
<212> TYPE: DNA
<213> ORGANISM: Artificial Sequence

```
<220> FEATURE:
<223> OTHER INFORMATION: Synthetic Construct; Primer

<400> SEQUENCE: 10
gcctcaattt acagtgtg                                                 18

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct; Primer

<400> SEQUENCE: 11
tgcttattca ttacagatgt t                                             21

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct; Primer

<400> SEQUENCE: 12
tgcaatttca cttatgatac cg                                            22

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct; Primer

<400> SEQUENCE: 13
agctcaggct ggccctttat                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct; Primer

<400> SEQUENCE: 14
gacctctttg tcctgcagca                                               20

<210> SEQ ID NO 15
<211> LENGTH: 22
<212> TYPE: DNA
<213> ORGANISM: Artificial Sequence
<220> FEATURE:
<223> OTHER INFORMATION: Synthetic Construct; Primer

<400> SEQUENCE: 15
gctttcgaag tttcagtagt ac                                            22
```

METHOD OF DETECTING RELATIVE RISK FOR THE ONSET OF ATOPIC DERMATITIS BY GENE SINGLE NUCLEOTIDE POLYMORPHISM ANALYSIS

TECHNICAL FIELD

The present invention relates to a method of discriminating relative risk for the morbidity of atopic dermatitis having specified gene polymorphism by calculating an odds ratio related to a combination of gene polymorphism of plural factors by analyzing single nucleotide polymorphism related to gene mutation of factors related to onset of atopic dermatitis, and a preventive and/or therapeutic agent of atopic dermatitis.

BACKGROUND ART

Atopic dermatitis is a chronic disease manifesting eczema with pruritus that repeats aggravation and remission as a major lesion (see the Journal of Allergy and Clinical Immunology (J. Allergy Clin. Immunol), 1999, vol. 104, S123). While the symptom of atopic dermatitis is diverse and the cause of the disease has not been elucidated yet, it is suspected that various substances such as natural substances including ticks, fur, feather, bacteria and fungi, foods such as egg and milk, and synthetic products such as chemical fibers and detergents may act as antigens. It is pointed out that skin barrier dysfunction caused by dry skin plays an important role in atopic dermatitis. In addition, it is recently suggested that stress is related to the onset of atopic dermatitis.

Topical steroids are usually used as remedies of atopic dermatitis (the Journal of Allergy and Clinical Immunology (J. Allergy Clin. Immunol), 1999, vol. 104, S123). However, it is necessary to exactly select the kind of the external use steroid preparation depending on severity of the disease and application sites and timing, and the symptom is reported to be aggravated by misusage. Side effects such as skin atrophy and rosacea-like dermatitis are known to occur by long term dosage of the external use steroid preparation, and a phenomenon called as rebound by which skin symptoms are remarkably aggravated may occur when administration of the preparation is improperly suspended.

Histamine antagonists and antiallergic agents are used today as the remedies of atopic dermatitis other than the external use steroid preparations. While the histamine antagonist is useful in the sense of partly alleviation of itch, it is usually considered not to lead to improvement of the skin dermatitis. The antiallergic agents such as tranilast, ketotifen, oxatomide and azelastine hydrochloride are ineffective or have little effect against atopic dermatitis, if any, and are usually used as auxiliary measures today. While an ointment of tacrolimus as an immunosuppressant has been recently developed as a remedy of atopic dermatitis (the Journal of Allergy and Clinical Immunology (J. Allergy Clin. Immunol), 1999, vol. 104, S126), emergence of side effect such as strong irritation on the skin has been apprehended.

Chymase inhibitors and anti-IgE antibodies have been reported as new candidates against atopic dermatitis. For example, it was elucidated that the chymase inhibitors such as SUN C8257 (Laboratory Investigation (Lab Invest), 2002, vol 82, p 789; and International Archives of Allergy and Immunology (Int Arch Allergy Immunol), 2002, vol. 128, p 229) and Y-40613 (Japanese Journal of Pharmacology (Jpn J Pharmacol), 2002, vol. 90, p 214) exhibit effectiveness in various mouse dermatitis models. Chymase is a chymotrypsin-like enzyme released from mast cells, and is shown to relate to processing of a stem cell factor for mast cell's own proliferation (Proceedings of the National Academy of Science of the United State of the America (Proc Natl Acad Sci USA), 1997, vol. 94, p 9017; and Biochemical and Biophysical Research Communications (Biochem Biophys Res Commun), 2002, vol. 290, p 1478) and random migration of the eosinophils. Inhibitors of chymase are suggested to be potentially useful as remedies of atopic dermatitis (Journal of Leukocyte Biology (J Leukoc Biol), 2000, vol. 67, p 585; and Biochemical Pharmacology (Biochem Pharmacol), 2002, vol. 64, p 1187). The anti-IgE antibody suppressed binding of blood IgE to mast cells. An example of the anti-IgE antibody is omalizumab, which is in an advanced stage of the clinical test against bronchial asthma and is approved as a medicine. Since a degranulation reaction of the mast cell via IgE is conjectured to play an important role in atopic dermatitis, application of omalizumab to atopic dermatitis has been expected (Monaldi Archives for Chest Diseases (Monaldi Arch Chest Dis), 2003, vol. 59, p 25).

Now, in terms of the fact that there are no remedies of atopic dermatitis that are satisfactory in both beneficial effects and side effects, these drugs may be possibly used in the clinical practice.

While atopic dermatitis is usually diagnosed by appearance and distribution of eczema of the skin, emergence of pruritus, if any, and clinical history, IgE level in the blood, familial onset of the disease and complications such as bronchial asthma and allergic rhinitis, if any, may be basis of diagnosis (Japanese Dermatological Association: Guideline of Therapy of Atopic Dermatitis, Journal of Japanese Dermatological Association, 2004, vol. 114, p 135). Accordingly, medication of atopic dermatitis usually include selection of appropriate drugs (one or more drugs) from the external use steroid preparations, anti-histamine agents, anti-allergic agents and immunosuppressants depending on severity of the disease and administration of the drugs after diagnosis mainly by finding of appearance. However, the cause of onset of atopic dermatitis is not clear at present, and selection of the remedies are not always based on scientific reasons. Rather, it mainly depends on the experience of medical specialists. Since patients of atopic dermatitis include non-allergic type patients and intrinsic type patients who do not exhibit elevation of the blood IgE level, accurate diagnosis becomes more difficult.

Since atopic dermatitis is frequently familial origin, involvement of hereditary factors has been pointed out for a long time. When the disease is hereditary, specifying causative genes not only offer valuable information on the development of remedies specific to the disease but also are quite useful in terms of effective therapy based on gene diagnosis. For example, when a causative gene of the disease is identified to enable a substance that inhibits the function of a protein encoded by the causative gene to be obtained, the substance is naturally considered to be useful as a remedy for the disease. Investigation of the structure and expression level of the causative gene for individuals permits risk for the onset of the disease (readiness of morbidity) to be predicted while it is related to estimation of the effect (susceptibility) of the remedy that targets the causative gene. Therefore, ideal therapies in accordance with the causes of the disease of the individual may be expected to be possible.

A method usually called as linkage analysis is used for analyzing the causative gene of the disease, and this method has been already applied in atopic dermatitis. For example, Lee et al. have analyzed (genome-wide linkage study) in the entire region of the genome of patients of atopic dermatitis, and have reported that 3q21 of the chromosome is a candidate of the causative region (Nature Genetics (Nat Genet), 2000, vol. 26, p 470). Cookson's group has shown possibility of 1q21, 17q25 and 20p as candidates of the causative regions (Nature Genetics (Nat Genet), 2001, vol. 27, p 372). However, the gene region targetable by this method is restricted, and it is a current situation that no specific causative genes have been identified.

As for a method of targeting genes other than linkage analysis, there is a method in which the specific gene that may be the causes of the disease is subjected to Single nucleotide polymorphism (SNPs) analysis. SNPs analysis has been applied to chymase, high affinity IgE receptor (FcεRIβ, IL-4 receptor and RANTES with respect to atopic dermatitis, and correlation between the disease and onset thereof has been reported. For example, Mao et al. (Lancet, 1996, vol. 48, p 1) have reported SNPs of 3255th nucleotide of the human mast cell chymase gene is correlated with onset of atopic dermatitis, while Shirakawa et al. (Nature Genetics (Nat Genet), 1994, vol. 7, p 125) have reported SNPs of 1343rd nucleotide of the high affinity IgE receptor gene is correlated with onset of atopic dermatitis. However, correlation between SNPs of these genes and onset of atopic dermatitis is not always clear, and there are opposed reports that atopic dermatitis is not correlated at all in the SNPs analysis of the same gene (Human Heredity (Hum Hered), 1998, vol. 48, p 271; Human Heredity (Hum Hered), 2001, vol. 51, p 177; and International Archives of Allergy and Immunology (Int Arch Allergy and Immunol), 1996, vol. 111, p 44). Therefore, the causative genes of atopic dermatitis are not concluded to be identified today.

DISCLOSURE OF INVENTION

Problems to be Solved by the Invention

While several candidate genes related to onset and/or development (susceptibility) of atopic dermatitis (may be abbreviated as AD hereinafter) have been proposed, little is known about interaction among them and which gene largely affects the development of the disease. While gene mutations of human mast cell chymase (abbreviated as MCC hereinafter), RANTES as a migration factor of eosinophils and human high affinity IgE receptor β-chain (abbreviated as FcεRIβ hereinafter) have been hitherto shown to be possibly related to the susceptibility of AD, interaction of genes and/or onset and development of AD related to these gene mutation have not been elucidated yet.

The problem to be solved by the present invention is to provide a detection and discrimination method of relative risk for the morbidity of AD from the analysis of major factors related to onset and development of AD and interaction among the genes; prediction of susceptibility of the AD patient to drugs based on the genes and a selection method of preventive and/or therapeutic agents of AD from which harmful reactions of chemicals have been eliminated; a method of determining diagnostic and therapeutic methods characterized in using the method of detecting the relative risk for the morbidity; and a diagnostic method and therapeutic method of AD based on the method of determining the diagnostic method and therapeutic method.

Means for Solving the Problems

The inventors of the present invention have analyzed, in intensive studies for solving the above-mentioned problems, the genotype of the single nucleotide polymorphism of allergy-related genes of each of the AD patient and normal person, i.e. which of the guanine-guanine homozygote, guanine-adenine heterozygote and adenine-adenine homozygote is the genotype of single nucleotide polymorphism of 3255th nucleotide of MCC gene (Sequence Table: SEQ ID NO: 1); which of guanine-guanine homozygote, guanine-adenine heterozygote and adenine-adenine homozygote is the genotype of the single nucleotide polymorphism of 1343rd nucleotide (Sequence Table: 1798th nucleotide of SEQ ID NO: 2) from the initiation codon (Sequence Table: 456 . . . 458 of SEQ ID NO: 2) of the FcεRIβ gene; which of guanine-guanine homozygote, guanine-adenine heterozygote and adenine-adenine homozygote is the genotype of single nucleotide polymorphism of −403rd nucleotide (Sequence Table: 556th nucleotide of SEQ ID NO: 3) at the upstream side counted from the transcription initiation site (Sequence Table: 959th nucleotide of SEQ ID NO: 3) of mRNA of RANTES gene; which of guanine-guanine homozygote, guanine-cytosine heterozygote and cytosine-cytosine homozygote is the genotype of single nucleotide polymorphism of the −28th nucleotide (Sequence Table: 931st nucleotide of SEQ ID NO: 3) at the upstream side counted from the transcription initiation site (Sequence Table: 959th nucleotide of SEQ ID NO: 3) of mRNA of the RANTES gene; or which of guanine-guanine homozygote, guanine-adenine heterozygote and adenine-adenine homozygote is the genotype of 4257th nucleotide of single nucleotide polymorphism of interleukin-13 (Sequence Table: SEQ ID NO: 4). The inventors have found that AD morbidity rate is different depending on the combination of genotypes of the single nucleotide polymorphism of two or more of allergy-related genes. The present invention has been completed through repeated studies.

The present invention relates to:

(1) A method of discriminating a relative risk for the morbidity of atopic dermatitis of a test subject comprising:

analyzing gene polymorphism of two or more of genes related to onset of atopic dermatitis using biogenic components collected from a statistically significant number of normal persons and patients of atopic dermatitis as test samples to determine relative ratios (percentages (%)) related to individual gene polymorphisms derived from the analysis; calculating an odds ratio according to specified gene polymorphism from the relative ratio; and using, as a discrimination criterion, a combination of polymorphism of two or more of genes showing a synergetically higher odds ratio than odds ratios according to individual gene polymorphisms;

(2) the method according to above (1), characterized in that one of two or more of the genes related to onset of atopic dermatitis is an MCC gene;

(3) the method according to above (2), characterized in that the gene related to onset of atopic dermatitis other than the MCC gene is one or more of the genes selected from a FcεRIβ gene, a RANTES gene and an interleukin-13 gene;

(4) the method according to above (1), comprising the step of determining an odds ratio of individual gene polymorphism in a combination of any two steps selected from steps (a) to (e) below:

(a) a step of analyzing gene polymorphism for determining which of guanine and adenine is the 3255th nucleotide of the nucleotide sequence represented by SEQ ID NO: 1 of the sequence table as the MCC gene extracted from a sample isolated from the human;

(b) a step of analyzing gene polymorphism for determining which of guanine and adenine is the 1343rd nucleotide from the initiation codon of the nucleotide sequence represented by SEQ ID NO: 2 of the sequence table as the FcεRIβ gene extracted from a sample isolated from the human;

(c) a step of analyzing gene polymorphism for determining which of guanine and adenine is the −403rd nucleotide at the upstream side counted from the transcription initiation site of mRNA of the nucleotide sequence represented by SEQ ID NO: 3 of the sequence table as the RANTES gene extracted from a sample isolated from the human;

(d) a step of analyzing gene polymorphism for determining which of guanine and cytosine is the −28th nucleotide at the upstream side counted from the transcription initiation site of mRNA of the nucleotide sequence represented by SEQ ID NO: 3 of the sequence table as the RANTES gene extracted from a sample isolated from the human; and (e) a step of analyzing gene polymorphism for determining which of guanine and adenine is the 4257th nucleotide of the nucleotide sequence represented by SEQ ID NO: 4 of the sequence table as the interleukin-13 gene extracted from a sample isolated from the human;

(5) the method according to above (4), characterized in that the two steps are a combination of steps (a) and (b), steps (a) and (c), steps (a) and (d), or steps (a) and (e);

(6) the method according to above (1), comprising the step of determining the odds ratio of individual gene polymorphism in a combination of any two steps selected from the steps of (g) to (k) below;

(g) a step of analyzing gene polymorphism for determining which of guanine-guanine homozygote, guanine-adenine heterozygote and adenine-adenine homozygote is the combination of the 3255th nucleotide of the nucleotide sequence represented by SEQ ID NO: 1 of the sequence table as the MCC gene extracted from a sample isolated from the human;

(h) a step of analyzing gene polymorphism for determining which of guanine-guanine homozygote, guanine-adenine heterozygote and adenine-adenine homozygote is the combination of the 1343rd nucleotide from the initiation codon of the nucleotide sequence represented by SEQ ID NO: 2 of the sequence table as the FcεRIβ gene extracted from a sample isolated from the human;

(i) a step of analyzing gene polymorphism for determining which of guanine-guanine homozygote, guanine-adenine heterozygote and adenine-adenine homozygote is the combination of the −403rd nucleotide at the upstream side counted from the transcription initiation site of the mRNA of the nucleotide sequence represented by SEQ ID NO: 3 of the sequence table as the RANTES gene extracted from a sample isolated from the human;

(j) a step of analyzing gene polymorphism for determining which of guanine-guanine homozygote, guanine-cytosine heterozygote and cytosine-cytosine homozygote is the combination of the −28th nucleotide at the upstream side counted from the transcription initiation site of mRNA of the nucleotide sequence represented by SEQ ID NO: 3 of the sequence table as the RANTES gene extracted from a sample isolated from the human; and (k) a step of analyzing gene polymorphism for determining which of guanine-guanine homozygote, guanine-adenine heterozygote and adenine-adenine homozygote is the combination of the 4257th nucleotide of the nucleotide sequence represented by SEQ ID NO: 4 of the sequence table as the interleukin-13 gene extracted from a sample isolated from the human;

(7) the method according to above (6), characterized in that the two steps are a combination of steps (g) and (h), steps (g) and (i), steps (g) and (j) or steps (g) and (k).

(8) the method according to (3) for judging the probability of relative risk for the morbidity against atopic dermatitis high when the combination of the 3255th nucleotide of the nucleotide sequence represented by SEQ ID NO: 1 of the sequence table as the MCC gene extracted from a sample isolated from the human is guanine-guanine homozygote, and the combination of the 1343rd nucleotide from the initiation codon of the nucleotide sequence represented by SEQ ID NO: 2 of the sequence table as the FcεRIβ gene extracted from a sample isolated from the human is the guanine-adenine heterozygote or adenine-adenine homozygote; or the combination of the −403rd nucleotide at the upstream side counted from the transcription initiation site of mRNA of the nucleotide sequence represented by SEQ ID NO: 3 of the sequence table as the RANTES gene is guanine-adenine heterozygote or adenine-adenine homozygote; or the combination of the −28th nucleotide at the upstream side counted from the transcription initiation site of mRNA of the nucleotide sequence represented by SEQ ID NO: 3 of the sequence table as the RANTES gene is the guanine-cytosine heterozygote or guanine-guanine homozygote; or the combination of the 4257th nucleotide of the nucleotide sequence represented by SEQ ID NO: 4 of the sequence table as the interleukin-13 gene is adenine-adenine homozygote or guanine-adenine heterozygote;

(9) a method of judging a test subject having gene polymorphism of a combination showing a value of 3.00 or more of an odds ratio calculated from the step according to any one of above (4) to (7) to be in a high relative risk for the onset and/or development of atopic dermatitis;

(10) a method of judging a test subject having gene polymorphism of a combination showing a value of 3.50 or more of an odds ratio calculated from the steps according to any one of above (4) to (7) to be in a high relative risk for the onset and/or development of atopic dermatitis;

(11) a method of judging a test subject having gene polymorphism of a combination showing a value of 4.00 or more of an odds ratio calculated from the steps according to any one of above (4) to (7) to be in a high relative risk for the onset and/or development of atopic dermatitis;

(12) a method of judging a test subject having gene polymorphism of a combination showing a value of 4.50 or more of an odds ratio calculated from the step according to any one of above (4) to (7) to be in a high relative risk for the onset and/or development of atopic dermatitis;

(13) a method of predicting effectiveness of a preventive agent and/or therapeutic agent of atopic dermatitis using the method according to any one of above (1) to (8);

(14) a method of selecting a preventive agent and/or therapeutic agent of atopic dermatitis using the method according to any one of above (1) to (8);

(15) a method of screening atopic dermatitis patients using the method according to any one of above (1) to (8);

(16) a method of screening atopic dermatitis patients for which effectiveness of a chymase preventive agent is predicted using the method according to any one of above (1) to (8);

(17) a diagnostic method of atopic dermatitis, which comprises using the method according to any one of above (1) to (8);

(18) a SNP chip for diagnosis of atopic dermatitis, which comprises using the method according to any one of above (1) to (8);

(19) a preventive and/or therapeutic method of atopic dermatitis by administering the preventive agent and/or therapeutic agent selected by the method according to above (14);

(20) a method of selecting preventive agents and/or therapeutic agents of atopic dermatitis, characterized in that the preventive agents and/or therapeutic agents are one or more agents selected from a chymase inhibitor, a agent for inhibiting binding between IgE and a receptor thereof, and an agent for inhibiting the function of an IgE receptor;

(21) the preventive and/or therapeutic method according to above (19), wherein the preventive agent and/or therapeutic agent is at least one selected from a chymase inhibitor, an agent for inhibiting binding between IgE and the receptor thereof, and an agent for inhibiting the function of an IgE receptor;

(22) a detection kit of gene polymorphism related to atopic dermatitis comprising the method defined in any one of above (1) to (8);

(23) a diagnosis kit of the patient of atopic dermatitis comprising the method defined in any one of above (1) to (8); and

(24) a kit for predicting effectiveness of the preventive agent and/or therapeutic agent comprising the method defined in any one of above (1) to (8).

Effect of the Invention

Relative morbidity risk of AD that has been impossible to distinctly predict from the analysis of one single gene nucleotide polymorphism in the prior art may be predicted with a high probability according to the method of the present invention. The present invention makes it possible to predict susceptibility of a patient to chemicals, and drugs suitable for the genotype of AD patients may be selected.

BRIEF DESCRIPTION OF THE DRAWINGS

FIG. 1 shows a method of calculating relative risk for the morbidity.

FIG. 2 shows a method of calculating the odds ratio.

BEST MODE FOR CARRYING OUT THE INVENTION

"Gene polymorphism" as used in the specification refers to polymorphism caused by substitution of one nucleotide of the DNA nucleotide sequence incised in the genome of an individual, or single nucleotide polymorphism (SNPs).

The term "gene" as used in the specification includes not only DNAs but also mRNAs and cRNAs corresponding to the DNAs. Accordingly, the gene of the present invention includes all of the DNAs, mRNAs, cDNAs and cRNAs.

The term "relative risk for the morbidity" as used in the specification refers to a ratio of the AD morbidity of a person having the AD risk factor to the AD morbidity of a person having no AD risk factor, and is also referred to "relative risk". "Relative risk for the morbidity" is detected by calculating the relative risk for the morbidity.

"Chymase" is a chymotrypsin-like serine protease present in granules of the mast cell. Chymase is preferably originates in the human mast cell. A preferable example of the gene of chymase originating in the human mast cell is that registered in a public database GenBank (NCBI) with an accession No. M64269. The nucleotide sequence of the chymase gene originating in the human mast cell is represented by SEQ ID NO: 1. The 3255th nucleotide in this nucleotide sequence is guanine (abbreviated as G hereinafter), and the allele of SNPs thereof is adenine (abbreviated as A hereinafter).

FcεRIβ is known to activate the mast cell, and relates to bronchial asthma. A preferable example of the FcεRIβ gene is a known sequence registered to GenBank (NCBI) with an accession No. M89796. The nucleotide sequence of the FcεRIβ gene is shown in SEQ ID NO: 2. The nucleotide corresponding to 1798th in this nucleotide sequence and 1343rd nucleotide (referred to 1343rd of the FcεRIβ gene in the present invention) counted from the initiation codon (Sequence Table: 456 . . . 458 of SEQ ID NO: 2) is G, and the allele thereof of SNPs is A.

RANTES is an abbreviation of "Regulated upon Activation, Normal T Cell Expressed, and Secreted (Schall, 1990)", and histamine is released from the basophiles to activate eosinophils. A preferable example of the human RANTES gene is a known sequence registered in GenBank (accession No.: S64885). The nucleotide sequence of the RANTES gene is shown in SEQ ID NO: 3. The −403rd nucleotide (Sequence Table: 556th of SEQ ID NO: 3; referred to −403rd of the RANTES gene hereinafter in the present invention) at the upstream side counted from the transcription initiation site (Sequence Table: 959th of SEQ ID NO: 3) of mRNA in this nucleotide sequence is A, and the allele of SNPs thereof is G. Human has a genotype of AA, AG (GA) or GG against this SNPs. The −28th nucleotide (Sequence Table: 931st of SEQ ID NO: 3; referred to −28th of the RANTES gene hereinafter in the present invention) at the upstream side counted from the transcription initiation site (Sequence Table: 959th of SEQ ID NO: 3) of mRNA in this nucleotide sequence is cytosine (abbreviated as C hereinafter), and the allele of SNPs thereof is G. Human has a genotype of CC, CG (GC) or GG against this SNPs.

Interleukin-13 (abbreviated as IL-13 hereinafter) has many actions related to so-called allergic factors such as regulation of IgE production and induction of expression of various adhesion factors, and acts as an effector molecule of asthma. IL-13 is known to express symptoms characteristic to allergic asthma such as respiratory tract hypersensitivity, eosinophilic inflammation and dysplasia of mucous membrane only by administering IL-13 to non-sensitized animals. A preferable example of the human IL-13 gene is a known sequence registered to GenBank (NCBI) with accession No: U31120. The nucleotide sequence of the IL-13 gene is shown by SEQ ID NO: 4. The 4257th nucleotide in this nucleotide sequence is G, and the allele of SNPs thereof is A. Human has a genotype of AA, AG (GA) or GG against this SNPs. Further, the amino acid (Sequence Table: 130th amino acid of SEQ ID NO:5) corresponding to the codon (Sequence Table: 4256 . . . 4258 of SEQ ID NO: 4) containing the gene polymorphism site (4247th nucleotide of SEQ ID NO: 4) in the amino acid sequence (Sequence Table: SEQ ID NO: 5) of the expressed protein of the IL-13 gene is Arg, and the amino acid corresponding to the codon containing the nucleotide (A) of the SNPs is Gln. Accordingly, the genotype of IL-13 may be analyzed based on the amino acid sequence of the expressed protein.

The phrase "analyze gene polymorphism" as used in the present invention refers to investigate what genotype the patient has with respect to polymorphism of the gene as an object of analysis, and is synonymous with investigating nucleotides (nucleotide sequence) at the site where polymorphism of a specified gene is included. In an example of the analysis of polymorphism of 3255th nucleotide (G/A) of the MCC gene (Sequence Table: SEQ ID NO: 1), the phrase means to investigate which of GG (homozygote of alleles both having G at 3255th nucleotide), GA (heterozygote of one allele with G at 3255th nucleotide and other allele with A at 3255th nucleotide) and AA (homozygote of alleles both having A at 3255th nucleotide) is the genotype of MCC in a sample extracted from a patient, for example in the lymphocyte of the patient. Likewise, in the analysis of polymorphism of 1343rd nucleotide (G/A) of the FcεRIβ gene (Sequence Table: SEQ ID NO: 2), the phrase means, for example, to investigate which of GG (homozygote of alleles both having G at 1343rd nucleotide), GA (heterozygote of one allele with G at 1343rd nucleotide and other allele with A at 1343rd nucleotide) and AA (homozygote of alleles both having A at 1343rd nucleotide) is the genotype of the FcεRIβ gene in the lymphocyte of the patient; in the analysis of polymorphism of −403rd nucleotide (G/A) of the RANTES gene (at the upstream side counted from the transcription initiation site of mRNA of the nucleotide sequence represented by Sequence Table: SEQ ID NO: 3), the phrase means, for example, to investigate which of GG (homozygote of alleles both having G at −403rd nucleotide), GA (heterozygote of one allele with G at −403rd nucleotide and other allele with A at −403rd nucleotide) and AA (homozygote of alleles both having A at −403rd nucleotide) is the genotype of the RANTES gene in the lymphocyte of the patient; in the analysis of polymorphism of −28th nucleotide (G/C) of the RANTES gene (upstream side counted from the transcription initiation site of mRNA of the nucleotide sequence represented by Sequence Table: SEQ ID NO: 3), the phrase means, for example, to investigate which of GG (homozygote of alleles both having G at −28th nucleotide), GC (heterozygote of one allele with G at −28th nucleotide and other allele with C at −28th nucleotide) and CC (homozygote of alleles both having C at −28th nucleotide) is the genotype of RANTES gene in the lymphocyte of the patient; in the analysis of polymorphism of 4257th nucleotide (G/A) of the IL-13 gene (Sequence Table: SEQ ID NO: 4), the phrase means, for example, to investigate which of GG (homozygote of alleles both having G at 4257th nucleotide), GA (heterozygote of one allele with G at 4257th nucleotide and other allele with A at 4257th nucleotide) and AA (homozygote of alleles both having A at 4257th nucleotide) is the genotype of the IL-13 gene in the lymphocyte of the patient; and, in the analysis of 130th amino acid (Arg/Gln) of IL-13 (Sequence Table: SEQ ID NO: 5), the phrase means, for example, to investigate which of Arg/Arg (the 130th amino acids are Arg in both alleles), Arg/Gln (one allele has Arg at 130th amino acid and other allele has Gln at 130th amino acid), and Gln/Gln (the 130th amino acids are Gln in both alleles) is the 130th amino acid of IL-13 in the lymphocyte of the patient.

The method of analyzing each gene polymorphism is not particularly restricted, and may be performed by detecting each gene polymorphism and by identifying each genotype. For detection of each gene polymorphism and identification of genotype, DNAs are extracted from a sample collected from a patient at first. While DNAs may be extracted by known methods such as extraction with a DNA extraction solution containing an anionic surfactant, commercially available DNA extraction kits such as IsoQuick kit (manufactured by ORCA Research Inc.), DNA Extraction Kit (manufactured by Shimadzu Rika Co.) and GeneBall Genome Preparation Kit (manufactured by Takara Bio Co) may be used.

Gene polymorphisms of such as MCC genome, FcεRIβ gene, RANTES gene or IL-13 gene are detected from the obtained sample that contains DNAs by known methods, for example the following methods to determine genotypes: (1) PCR-RFLP (restriction fragment length polymorphism) method; (2) PCR-SSCP method (single strand conformation polymorphism) method; (3) ASO (allele specific oligonucleotide) hybridization method; (4) ARMS (amplification refracting mutation system) method; (5) invader method; (6) ARMS (amplification refracting mutation system) method; (7) MALDI-TOF/MS (matrix assisted laser desorption-time of flight/mass spectrometry) method; (8) method using DNA chip or micro-array; (9) LAMP (loop-mediated isothermal amplification) method; (10) RT-LAMP (reverse transcription-loop mediated isothermal amplification) method; (11) ICAN (isothermal and chimeric primer-initiated amplification of nucleic acids) method; (12) UCAN (SNP typing) method; (13) direct sequence method; (14) cycling probe method; (15) ALBUM (aldehyde-linker based ultra-sensitive mismatch scanning) method; (16) dot hybridization method; (17) denaturing gradient gel electrophoresis (referred to "DGGE" hereinafter); (18) RNase cleavage method (19) DOL (dye-15' labeled oligonucleotide ligation) method; (20) TDI (template-directed dye terminator incorporation) method; (21) TaqMan-PCR method; (22) molecular beacon method; (23) DASH (dynamic allele specific hybridization) method; and (24) ECA (electrochemical array) method. Detection of gene polymorphism and identification of genotype are not restricted to the above-mentioned methods, and other known methods for detecting gene polymorphism may be used in the present invention. In the method according to the present invention, one of the methods for identifying gene polymorphism may be used alone, or a combination of plural methods may be used.

The method using PCR-RFLP as one of the favorable embodiments of the present invention will be shown in the example to be described hereinafter. In the PCR-RFLP method, gene polymorphism is detected from the difference of the length of DNA fragments formed by digestion with a restriction enzyme, when a gene polymorphism site is included in the site recognized by the restriction enzyme. Specifically, the DNA fragment containing the polymorphism site is amplified by PCR, the amplified DNA is cleaved with a restriction enzyme, and the sizes of the cleaved DNA fragments are analyzed by electrophoresis. An oligonucleotide having a length of 15 to 30 mer is preferable as a PCR primer for amplifying about 0.05 to 4 kb fragments containing the polymorphism site.

Gene Polymorphism is preferably analyzed by a method using the PCR method (for example PCR-RFLP method) when the amount of the sample is small in terms of sensitivity and accuracy of detection. Any one of the above-mentioned methods may be applied after amplifying (including amplification of a part of the region of the nucleotide sequence) the sample in advance by a gene amplification method such as the PCR method.

Examples of DNAs amplified in the above-mentioned analytical method include DNAs having complementary sequences at a given region (partial DNA region) including the polymorphism site of the gene containing polymorphism as an object of analysis. The primer or probe is preferably designed depending on desired SNPs, and examples of the primer and probe include the primer or probe which is designed so that the primer or probe contains a complementary sequence to a given region (partial DNA region) containing the polymorphism site in the gene having polymorphism to be analyzed, and so that the DNA fragment containing the polymorphism site is selectively amplified. The oligonucleotide of the primer or probe preferably has a length enough for exhibiting the function of the oligonucleotide, or a length of about 15 to 30 bases. The primer may have a little mismatch to the sequence as a template, so long as the primer specifically hybridizes to the region to be amplified so that a desired DNA fragment is amplified. The probe may have also a little mismatch to the sequence to be detected, so long as specific hybridization with the sequence to be detected is possible. The extent of mismatch is from 1 to several nucleotides, preferably 1 to 5 nucleotides, and more preferably from 1 to 3 nucleotides.

Examples of such primer include: primers comprising nucleotide sequences represented respectively by SEQ ID NOs: 6 and 7 when polymorphism of 3255th nucleotide (G/A) of MCC gene (Sequence Table: SEQ ID NO: 1) is to be analyzed; primers comprising nucleotide sequences represented respectively by SEQ ID NOs: 8 and 9 when polymorphism of 1343rd nucleotide (G/A) of FcεRIβ gene (Sequence Table: SEQ ID NO: 2) is to be analyzed; primers comprising nucleotide sequences represented respectively by SEQ ID NOs: 10 and 11 when polymorphism of −403rd nucleotide (G/A) of RANTES gene (Sequence Table: SEQ ID NO: 3) is to be analyzed; primers comprising nucleotide sequences represented respectively by SEQ ID NOs: 12 and 13 when polymorphism of −28th nucleotide (G/C) of RANTES gene (Sequence Table: SEQ ID NO: 3) is to be analyzed; and primers comprising nucleotide sequences represented respectively by SEQ ID NOs: 14 and 15 when polymorphism of 4257th nucleotide (G/A) of IL-13 gene (Sequence Table: SEQ ID No: 4) is to be analyzed.

The above-mentioned primer or probe is only an example, and a part of the nucleotide sequence of the primer or probe may be modified within a limit that does not interfere with desired amplification reaction of the primer or probe. The term "modification of a part of" refers to deletion, substitution and/or addition of a part of the nucleotide sequence. The number of the nucleotide related to such modification is, for example, from 1 to 7, preferably from 1 to 5 and more preferably from 1 to 3. This modification may be principally applied to portions other than the nucleotide related to the polymorphism sites.

The primer or probe used for SNPs analysis may be synthesized by known methods such as phosphodiester method. References may be made, for example, to Molecular Cloning, Third Edition, Cold Spring Harbor Laboratory Press, New York, with respect to design and synthesis of the primer or probe for the analysis of SNPs.

The sample for the analysis of SNPs may be prepared by using known extraction and purification methods from the blood, skin cells, mucous membrane cells, hair or urine of the test subject. Genome DNAs having an arbitrary length may be used so long as they contain genes to be used as an object for the analysis of SNPs. The gene as an object of the SNPs analysis may be not in a perfect state (a gene having an intact full length) in the sample. Instead, if the polymorphism site to be analyzed exists therein, it may be a fragment of DNA or a partial DNA.

Polymorphism of each gene may be analyzed using mRNA as a transcription product of the gene to be analyzed. For example, mRNA of the gene as an object for the analysis is extracted from the above-mentioned sample such as blood derived from a test subject, and purified. Then, SNPs analysis can be carried out by using mRNA as a starting material by applying a method of using Northern blot method (Molecular Cloning, Third Edition, 7.42, Cold Spring Harbor Laboratory Press, New York), dot blot method (Molecular Cloning, Third Edition, 7.46, Cold Spring Harbor Laboratory Press, New York), RT-PCR method (Molecular Cloning, Third Edition, 8.46, Cold Spring Harbor Laboratory Press, New York) or DNA chip (DNA array) method.

When polymorphism involves changes of amino acids, for example in IL-13, analysis of polymorphism is possible using an expression product of the gene to be analyzed. In this case, a partial protein or partial peptide may be used as the sample for SNPs analysis so long as it contains an amino acid (Arg or Gln) corresponding to the polymorphism site. A method of directly assaying the amino acids at the polymorphism site or an immunological method may be used in this case. Known amino acid sequence analysis method such as Edman method may be used in the former, while a method using a monoclonal or polyclonal antibody having bonding activity specific to the expression product of the gene, for example an enzyme-linked immunosorbent assay method (ELISA method), radio-immunoassay, immunoprecipitation method or immunodiffusion method, may be used in the latter.

Information on polymorphism obtained as described above may be statistically totaled and used for diagnosis of AD, detection and discrimination of the relative risk for the morbidity and selection of remedies.

The odds ratio and relative risk for the morbidity of atopic dermatitis by SNPs have the same meaning in the present invention. In other words, the relative risk for the morbidity as a result of having a risk factor is represented by the ratio (relative risk for the morbidity) of AD morbidity of a person having the risk factor to AD morbidity of a person having no risk factor (corresponds to SNPs in the present invention). On the other hand, the odds ratio is represented by a ratio of the probability of emergence of an event to the probability of non-emergence of the event. Here, the numbers of the persons in an onset group having the risk factor and in a normal group having the risk factor are represented by a and b, respectively, and the numbers of the persons in an onset group having no risk factor and in a normal group having no risk factor are represented by c and d, respectively. Then, the relative risk for the morbidity is represented by $a(c+d)/c(a+b)$ as shown in FIG. 1.

On the other hand, the odds ratio is represented by $ad/bc$ (FIG. 2).

While the morbidity risk due to the risk factor may be naturally expressed by determining the relative risk for the morbidity, the original parent population is not reflected on the number of the extracted samples. Therefore, determining the relative risk for the onset is not always to determine the true morbidity risk. When the number of the morbid patients is small relative to the total population ($a \ll b$, $c \ll d$) as in atopic dermatitis, the relative risk for the morbidity is represented by $a(c+d)/c(a+b) \approx ad/bc$, and the odds ratio is equal to the relative risk for the morbidity.

When a combination of genotypes with an odds ratio of about 3 or more, preferably about 3.5 or more, more preferably about 4 or more and particularly about 4.5 or more is detected from information on SNPs obtained above, the morbidity risk of AD or onset of AD may be judged to be high. More specifically, when any one or more of combinations of genotypes of (a) to (e) is detected, the morbidity risk of AD or onset of AD may be judged to be high:

(a) a combination between a homozygote whose genotype of SNPs of 3255th nucleotide of MCC gene (Sequence Table: SEQ ID NO: 1) is GG and a homozygote or heterozygote whose genotype of SNPs of 1343rd (1343rd of SEQ ID NO: 2) nucleotide of FcεRIβ gene (Sequence Table: SEQ ID NO: 2) is AA or AG, respectively;

(b) a combination between a homozygote whose genotype of SNPs of 3255th (3255 th of SEQ ID NO: 1) nucleotide of MCC gene (Sequence Table: SEQ ID NO: 1) is GG and a homozygote or heterozygote whose genotype of SNPs of −403rd nucleotide of RANTES gene (Sequence Table: SEQ ID NO: 3) is AA or AG, respectively;

(c) a combination between a homozygote whose genotype of SNPs of 3255th nucleotide of MCC gene (Sequence Table: SEQ ID NO: 1) is GG and a homozygote or heterozygote whose genotype of SNPs of −28th nucleotide of RANTES gene (Sequence Table: SEQ ID NO: 3) is GG or CG, respectively;

(d) a combination between a homozygote whose genotype of SNPs of 3225th nucleotide of MCC gene (Sequence Table: SEQ ID NO: 1) is GG and a homozygote or heterozygote whose genotype of SNPs of 4275th nucleotide of IL-13 gene (Sequence Table: SEQ ID NO: 4) is AA or AG, respectively; and (e) a combination of a homozygote whose genotype of SNPs of 3255th nucleotide of MCC gene (Sequence Table: SEQ ID NO: 1) is GG and Arg/Arg or Arg/Gln of 130th amino acid of IL-13 (Sequence Table: SEQ ID NO: 5).

The degree of the morbidity risk of AD in the future (probability of onset) or the risk of onset may be predicted by checking morbidity risk of AD, and certification of AD and confirmation of the symptom may be possible based on an objective index of the genotype. In other words, the diagnostic method of the present invention makes it possible to evaluate the relative risk for the morbidity of AD, discrimination of morbidity of AD, and confirmation of the symptom. It is clinically quite significant that evaluation of the relative risk for the morbidity may be possible, because indication of the relative risk for the morbidity in advance serves for primary prevention of AD to make it possible to prepare appropriate preventive measures.

Information obtained by the diagnostic method of the present invention may be applied for selection of appropriate therapeutic method, improvement of prognosis, improvement of the quality of life of the patient and reduction of the relative risk for the morbidity.

When an environmental factor is correlated with administered drugs by implementing the diagnostic method of the present invention, for example, reduction of the onset of AD by improving the environmental factor and selection of appropriate medication may be possible based on this information. For example, when the chymase inhibitor is approved to be effective for a patient having a genotype in which single nucleotide polymorphism of 3255th nucleotide of the MCC gene is, for example, GG homozygote, the chymase inhibitor may be administered using the genotype as an index. Likewise, a drug effective for a genotype of single nucleotide polymorphism of another gene, for example a drug for inhibiting binding of IgE and a receptor thereof or a drug for suppressing the function of the RANTES or IL-13 gene may be selected as a remedy. Examples of the chymase inhibitor include those described above as well as SUN C8257. Examples of the IgE inhibitors include an antibody IgE and omalizumab. An example of the RANTES inhibitor is Met-RANTES. An example of the IL-13 inhibitor is CAT-354 as a neutralizing antibody.

Gene therapy of AD may take advantage of gene information on onset of AD obtained in the present invention. For example, when polymorphism to be analyzed is found to be a genotype that enhances onset risk of AD as a result of applying the diagnostic method of the present invention, the symptom of AD may be alleviated, onset of AD may be suppressed and onset risk may be reduced by introducing a gene having a genotype of low onset risk into the body of the patient and by permitting the gene to be expressed in the body. The same effect may be expected by introducing an antisense strand corresponding to mRNA of a gene having a genotype of high onset risk in order to suppress expression of the mRNA.

The gene or antisense strand may be introduced, for example, by using a plasmid or virus vector for introducing the gene, or by electroporation (Potter, H. et al., Proc. Natl, Acad. Sci. U.S.A., 81, 7161-7165 (1984)), ultrasonic microbubble (Lawrie, A. et al., Gene Therapy, 7, 2023-2027 (2000)), lipofection (Felgner, P. L. et al., Proc. Natl, Acad. Sci. U.S.A., 84, 7413-7417 (1984)) and micro-injection (Graessmann, M. & Graessmann, A., Proc. Natl, Acad. Sci. U.S.A., 73, 366-370 (1976)). Desired genes may be directly (in vitro method) or indirectly (ex vivo method) introduced into the body by using these methods.

The present invention also provides a gene polymorphism detection kit or AD diagnosis kit for discriminating the morbidity risk of AD, and the kit includes the probe or primer for detecting single nucleotide polymorphism of the above-mentioned AD-related genes.

The present invention also provides a diagnosis chip of atopic dermatitis on which DNAs that hybridize with AD-related genes including single nucleotide polymorphism is fixed. The AD-related genes including single nucleotide polymorphism is the above-mentioned AD-related gene, and DNAs that that hybridize with AD-related genes including single nucleotide polymorphism are nucleotide sequences that hybridize with respective SNPs of the above-mentioned AD-related gene.

While the present invention is described in more detail below with reference to Examples, the present invention is by no means restricted to these Examples.

Abbreviations used in Examples are as follows.
A: adenine
C: cytosine
G: guanine
T thymine Example 1

SNPs Analysis of MCC Gene of AD Patient (Methods)

SNPs of 3255th nucleotide of the MCC gene was analyzed using 359 Japanese AD patients and 112 Japanese normal persons. Peripheral blood lymphocytes were collected from each person, DNA was extracted with IsoQuick kit (manufactured by ORCA Research Inc.), and SNPs of the MCC gene was analyzed by PCR-RFLP method. The following primers were used for the analysis, and DNAs containing 3255th G/A of the MCC gene were amplified by the PCR method. Primes:

```
5'-CAGAGTCTAAGTCACATGACC-3'    (Sequence Table:
                                SEQ ID NO: 6)

5'-TGACCAGAGTGATCCACTCC-3'     (Sequence Table:
                                SEQ ID NO: 7)
```

Amplified each DNA was digested with restriction enzyme BstXI, and cleaved DNA fragments were stained with ethidium bromide after electrophoresis using 4% agarose gel for analysis. The analytical condition was selected so that the proportion is significantly higher in the AD patient than in the normal person in the combination of heterozygote and homozygote or in homozygote alone. In data analysis, the combination of the data of homozygote and heterozygote and the data of the other homozygote were compared between the AD patients and normal persons. SNP of 3255th nucleotide of the MCC gene was analyzed between AA+AG and GG. SPSS program version 10.0 was used for the contingency table analysis and calculation of the odds ratio, 95% confidence interval and P-value (significance value: P-value was calculated using $\chi^2$ test or Fisher's exact test).

(Results)

The 3225th nucleotide sequence of the MCC gene was analyzed for the AD patients and normal persons by the PCR-RFLP method, and was classified into persons having GG genotype and persons having the other (GG+AA) genotype. The results showed that, although the person having the GG genotype showed higher AD morbidity rate than the person having AG+AA genotype (Table 1), the odds ratio (1.88, p<0.004) of the former was not always higher than the odds ratio of the latter. While the results coincide with the result of a published report (Lancet, 1996, vol. 48, p 1), another report described different results (Human Heredity (Hum Hered), 1998, vol. 48, p 271, and Human Heredity (Hum Hered), 2001, vol. 51, p 177).

Tables 1 to 5 show association study of AD and single gene polymorphism of MCC gene, FcεRIβ chain gene, RANTES-403 gene, RANTES-28 gene and IL-13 gene, respectively, in Examples 1 to 5.

TABLE 1

| | | Mcc 3255 G/A genotype | | | | |
|---|---|---|---|---|---|---|
| | n | AA (ratio) | AG (ratio) | GG (ratio) | Odds ratio* (95% CI) | Significant difference |
| normal person | 112 | 14 (13%) | 54 (48%) | 44 (39%) | | |
| AD patient | 359 | 15 (4%) | 147 (41%) | 197 (55%) | 1.88 (1.22-2.90) | P < 0.004 |

*AA + AG vs GG

Example 2

SNPs Analysis of FcεRIβ Gene of AD Patient (Methods)

SNPs of 1343rd nucleotide of the FcεRIβ gene was analyzed using 395 Japanese AD patients and 175 Japanese normal parsons. Peripheral blood lymphocytes were sampled from each person, DNA was extracted with IsoQuick kit (manufactured by ORCA Research Inc.), and SNPs of the FcεRIβ gene was analyzed by the PCR-RFLP method. The following primers were used for the analysis, and DNAs containing 1343 A/G of the FcεRIβ gene was amplified.

```
5'-CAGAATGTTCTCATGACTGAATTG-3'    (Sequence Table:
                                   SEQ ID NO: 8)

5'-CAAGTACAGAGCAGACAACTG-3'       (Sequence Table:
                                   SEQ ID NO: 9)
```

Amplified each DNA was digested with restriction enzyme RsaI, and cleaved DNA fragments were stained with ethidium bromide after electrophoresis using 4% agarose gel for analysis. The analytical condition was selected so that the proportion is significantly higher in the AD patient than in the normal person in the combination of heterozygote and homozygote or in homozygote alone. In data analysis, the combination of the data of homozygote and heterozygote and the data of the other homozygote were compared between the AD patients and normal persons. SNPs of 1343rd nucleotide of the FcεRIβ gene was analyzed between AA+AG genotype and GG genotype. SPSS program version 10.0 was used for the contingency table analysis and calculation of the odds ratio, 95% confidence interval and P-value (significance value: P-value was calculated using $\chi^2$ test or Fisher's exact test).

(Results)

The 1343rd nucleotide sequence of the FcεRIβ gene was analyzed for the AD patients and normal persons by the PCR-RFLP method, and was classified into persons having GG genotype and persons having the other (AG+AA) genotype. The result showed that, although AD morbidity rate was higher in the person having AG+AA genotype than in the person having GG genotype (Table 2), the odds ratio (1.59, p<0.028) of the former was not always higher than the odds ratio of the latter.

TABLE 2

| | | FcεRIβ 1343 A/G genotype | | | | |
|---|---|---|---|---|---|---|
| | n | AA (ratio) | AG (ratio) | GG (ratio) | Odds ratio* (95% CI) | Significant difference |
| Normal person | 175 | 4 (2%) | 33 (19%) | 138 (79%) | | |
| AD patient | 395 | 16 (4%) | 102 (26%) | 277 (70%) | 1.59 (1.04-2.42) | P < 0.028 |

*AA + AG vs GG

Example 3

SNPs Analysis of RANTES-403 Gene of AD Patient (Methods)

SNPs of −403rd nucleotide of the RANTES gene was analyzed using 515 Japanese AD patients and 177 Japanese normal persons. Peripheral blood lymphocytes were collected from each person, DNA was extracted with IsoQuick kit (manufactured by ORCA Research Inc.), and SNPs of the RANTES gene was analyzed by PCR-RFLP method. The following primers were used for the analysis, and DNAs containing −403 G/A of the RANTES gene were amplified by the PCR method. Primes:

```
5'-GCCTCAATTTACAGTGTG-3'          (Sequence Table:
                                   SEQ ID NO: 10)

5'-TGCTTATTCATTACAGATGTT-3'       (Sequence Table:
                                   SEQ ID NO: 11)
```

Amplified each DNA was digested with restriction enzyme MaeIII, and cleaved DNA fragments were stained with ethidium bromide after electrophoresis using 4% agarose gel for analysis. The analytical condition was selected so that the proportion in the AD patient is significantly higher than in the normal person in the combination of heterozygote and homozygote or in homozygote alone. In data analysis, the combination of the data of homozygote and heterozygote and the data of the other homozygote were compared between the AD patients and normal persons. SNPs of −403rd nucleotide of the RANTES gene was analyzed between persons having AA+AG genotype and persons having the GG genotype. SPSS program version 10.0 was used for the contingency table analysis and calculation of the odds ratio, 95% confidence interval and P-value (significance value: P-value was calculated using $\chi^2$ test or Fisher's exact test).

(Results)

The −403rd nucleotide sequence of the RANTES gene was analyzed for the AD patients and normal persons by the PCR-RFLP method, and was classified into persons having AA+AG genotype and persons having the other (GG) genotype. The results showed that, although the person having AA+AG nucleotide sequence showed higher AD morbidity rate than the person having GG nucleotide sequence (Table 3), the odds ratio (1.42, p<0.043) of the former was not always higher than the odds ratio of the latter.

TABLE 3

| | | RANTES −403 A/G genotype | | | | |
| --- | --- | --- | --- | --- | --- | --- |
| | n | AA (ratio) | AG (ratio) | GG (ratio) | Odds ratio* (95% CI) | Significant difference |
| Normal person | 177 | 22 (12%) | 67 (38%) | 88 (50%) | | |
| AD patient | 515 | 64 (12%) | 240 (47%) | 211 (41%) | 1.42 (1.01-2.01) | P < 0.043 |

*AA + AG vs GG

TABLE 4

| | | RANTES −28 C/G genotype | | | | |
| --- | --- | --- | --- | --- | --- | --- |
| | n | GG (ratio) | GC (ratio) | CC (ratio) | Odds ratio* (95% CI) | Significant difference |
| Normal person | 177 | 7 (4%) | 40 (23%) | 130 (73%) | | |
| AD patient | 389 | 8 (2%) | 153 (39%) | 228 (59%) | 1.95 (1.32-2.88) | P < 0.001 |

*GG + GC vs CC

Example 4

SPNs Analysis of RANTES −28th Gene of AD Patient (Methods)

SNPs of −28th nucleotide of the RANTES gene was analyzed using 389 Japanese AD patients and 177 Japanese normal persons. Peripheral blood lymphocytes were collected from each person, DNA was extracted with IsoQuick kit (manufactured by ORCA Research Inc.), and SNPs of the RANTES gene was analyzed by PCR-RFLP method. The following primers were used for the analysis, and DNAs containing −28 G/C of the RANTES gene were amplified by the PCR method. Primes:

```
5'-TGCAATTTCACTTATGATACCG-3'    (Sequence Table:
                                 SEQ ID NO: 12)
5'-AGCTCAGGCTGGCCCTTTAT-3'      (Sequence Table:
                                 SEQ ID NO: 13)
```

Amplified each DNA was digested with restriction enzyme Mn1I, and cleaved DNA fragments were stained with ethidium bromide after electrophoresis using 4% agarose gel for analysis. The analytical condition was selected so that the proportion in the AD patient is significantly higher in the normal person in the combination of heterozygote and homozygote or in homozygote alone. In data analysis, the combination of the data of homozygote and heterozygote and the data of the other homozygote were compared between the AD patients and normal persons. SNPs of −28th nucleotide of the RANTES gene was analyzed between GG+GC and CC. SPSS program version 10.0 was used for the contingency table analysis and calculation of the odds ratio, 95% confidence interval and P-value (significance value: P-value was calculated using $\chi^2$ test or Fisher's exact test).

(Results)

The −28th nucleotide sequence of the RANTES gene was analyzed for the AD patients and normal persons by the PCR-RFLP method, and was classified into persons having GG+CC genotype and persons having the other (CC) genotype. The results showed that, although the person having GG+GC genotype showed higher AD morbidity rate than the person having CC genotype (Table 4), the odds ratio (1.95, p<0.001) of the former was not always higher than the odds ratio of the latter.

Example 5

SNPs Analysis of IL-13 Gene of AD Patient (Methods)

SNPs of 4257th nucleotide of the IL-13 gene was analyzed using 245 Japanese AD patients and 174 Japanese normal persons. Peripheral blood lymphocytes were collected from each person, DNA was extracted with IsoQuick kit (manufactured by ORCA Research Inc.), and SNPs of the IL-13 gene was analyzed by PCR-RFLP method. The following primers were used for the analysis, and DNAs containing 4257 G/A of the IL-13 gene were amplified by the PCR method. Primes:

```
5'-GACCTCTTTGTCCTGCAGCA-3'     (Sequence Table:
                                SEQ ID NO: 14)
5'-GCTTTCGAAGTTTCAGTAGTAC-3'   (Sequence Table:
                                SEQ ID NO: 15)
```

Amplified each DNA was digested with restriction enzyme ScaI, and cleaved DNA fragments were stained with ethidium bromide after electrophoresis using 4% agarose gel for analysis. The analytical condition was selected so that the proportion in the AD patient is significantly higher than in the normal person in the combination of heterozygote and homozygote or in homozygote alone. In data analysis, the combination of the data of homozygote and heterozygote and the data of the other homozygote were compared between the AD patients and normal persons. SNPs of the IL-13 gene was analyzed between persons having AG+AA genotype and persons having GG genotype. SPSS program version 10.0 was used for the contingency table analysis and calculation of the odds ratio, 95% confidence interval and P-value (significance value: P-value was calculated using $\chi^2$ test or Fisher's exact test).

(Results)

The 4257th nucleotide sequence of the IL-13 gene was analyzed for the AD patients and normal persons by the PCR-RFLP method, and was classified into persons having GG genotype and persons having the other (AG+AA) genotype. The results showed that, although the person having AG+AA genotype showed higher AD morbidity rate than the person having GG genotype (Table 5), the odds ratio (1.79, p<0.004) of the former was not always higher than the odds ratio of the latter.

TABLE 5

| | n | GG (ratio) | AG (ratio) | AA (ratio) | Odds ratio* (95% CI) | Significant difference |
|---|---|---|---|---|---|---|
| Normal person | 174 | 96 (55%) | 63 (36%) | 15 (9%) | | |
| AD patient | 245 | 100 (41%) | 120 (49%) | 25 (10%) | 1.79 (1.21-2.64) | P < 0.004 |

IL-13 4257 A/G genotype

*AA + AG vs GG

Example 6

SNPs Analysis of MCC Gene and FcεRIβ Gene of AD Patient (Methods)

Peripheral blood lymphocytes were collected from 242 Japanese AD patients and 110 Japanese normal persons, and SNPs of the MCC gene and SNPs of the FcεRIβ gene were analyzed by the PCR-RFLP methods as in the method described in Examples 1 and 2. The combination of homozygote and heterozygote, and the other heterozygote derived in Examples 1 and 2 were respectively selected as the analysis condition, and the data were analyzed by comparing the data, in which the combination of homozygote and heterozygote is combined with the other homozygote respectively, between the AD patient and normal person. The result of analysis of a combination of a person having AA+AG genotype as the 3255th nucleotide of the MCC gene that shows the highest odds ratio and a person having GG genotype as the 1343rd nucleotide of the FcεRIβ gene, and the result of analysis of a combination of a person having GG genotype as the 3255th nucleotide of the MCC gene and a person having AA+AG genotype as the 1343rd nucleotide of the FcεRIβ gene are shown for the SNPs of the MCC gene and the FcεRIβ gene. SPSS program version 10.0 was used for the contingency table analysis and calculation of the odds ratio, 95% confidence interval and P-value (significance value: P-value was calculated using $\chi^2$ test or Fisher's exact test).

(Results)

SNPs of 3255th nucleotide of the MCC gene and SNPs of 1343rd nucleotide of the FcεRIβ gene were analyzed for AD patients and normal persons. The test subjects were classified into those having allele of each gene of GG and the others (allele of each gene of AG+AA), and AD morbidity rate was determined in each combination of respective classified groups to determine the odds ratio. The results showed that AD morbidity rate was high in the group (N=54) having GG genotype as SNPs of 3255th nucleotide of the MCC gene and having SNPs other than GG (Ag or AA) genotype of 1343rd nucleotide of the FcεRIβ gene. The odds ratio for the group (N=122) having SNPs other than GG (Ag or AA) genotype of the MCC gene and SNPs of GG genotype of the FcεRIβ gene was 4.82 (p<0.001) as shown in Table 6.

Example 7

SNPs Analysis of MCC Gene and RANTES Gene of AD Patient (Methods)

Peripheral blood lymphocytes were collected from 354 Japanese AD patients and 111 Japanese normal persons, and SNPs of the MCC gene and SNPs of the RANTES gene (−403rd nucleotide) were analyzed by the PCR-RFLP methods as in the method described in Examples 1 and 3. The combination of homozygote and heterozygote, and the other heterozygote derived in Examples 1 and 3 were selected as the analysis condition, and the data were analyzed by comparing the data, in which the combination of homozygote and heterozygote is combined with the other homozygote respectively, between the AD patient and normal person. The result of analysis of a combination of a person having AA+AG genotype as the 3255th nucleotide of the MCC gene that shows the highest odds ratio and a person having GG genotype as the −403rd nucleotide of the RANTES gene, and the result of analysis of a combination of a person having GG genotype as the 3255th nucleotide of the MCC gene and a person having AA+AG genotype as the −403rd nucleotide of the RANTES gene are shown for the SNPs of the MCC gene and the −403rd RANTES gene. SPSS program version 10.0 was used for the contingency table analysis and calculation of the odds ratio, 95% confidence interval and P-value (significance value: P-value was calculated using $\chi^2$ test or Fisher's exact test).

(Results)

SNPs of 3255th nucleotide of the MCC gene and SNPs of −403rd nucleotide of the RANTES gene were analyzed for AD patients and normal persons. The test subjects were classified into those having allele of each gene of GG genotype and the others (allele of each gene of AG+AA genotype), and AD morbidity rate was determined in each combination of respective classified groups to determine the odds ratio. The results showed that AD morbidity rate was high in the group (N=128) having GG genotype as SNPs of 3255th nucleotide of the MCC gene and having SNPs other than GG (Ag or AA) genotype of −403rd nucleotide of the RANTES gene. The odds ratio for the group (N=93) having SNPs other than GG (Ag or AA) genotype of the MCC gene and SNPs of GG genotype of −403rd nucleotide of the RANTES gene was 2.48 (p<0.003) as shown in Table 7.

TABLE 6

| MCC 3255 genotype | FcεRIβ 1343 genotype | n | normal person | AD patient | odds ratio (95% CI) | significant difference |
|---|---|---|---|---|---|---|
| AA + AG | GG | 122 | 51 (42%) | 71 (58%) | | |
| GG | AA + AG | 54 | 7 (13%) | 47 (87%) | 4.82 (2.02-11.53) | P < 0.001 |

TABLE 7

| MCC 3255 genotype | RANTES -403 genotype | n | Normal person | AD patient | Odds ratio (95% CI) | Significant difference |
|---|---|---|---|---|---|---|
| AA + AG | GG | 93 | 36 (39%) | 57 (61%) | | |
| GG | AA + AG | 128 | 26 (20%) | 102 (80%) | 2.48 (1.36-4.51) | P < 0.003 |

Example 8

SNPs Analysis of MCC Gene and RANTES −28 Gene of AD Patient (Methods)

Peripheral blood lymphocytes were collected from 250 Japanese AD patients and 112 Japanese normal persons, and SNPs of the MCC gene and SNPs of the RANTES gene (−28th nucleotide) were analyzed by the PCR-RFLP methods as in the method described in Examples 1 and 4. The combination of homozygote and heterozygote, and the other heterozygote derived in Examples 1 and 4 were selected as the analysis condition, and the data were analyzed by comparing the data, in which the combination of homozygote and heterozygote is combined with the other homozygote respectively, between the AD patient and normal person. The result of analysis of a combination of a person having AA+AG genotype as the 3255th nucleotide of the MCC gene that shows the highest odds ratio and a person having CC genotype as the −28th nucleotide of the RANTES gene, and the result of analysis of a combination of a person having GG genotype as the 3255th nucleotide of the MCC gene and a person having GG+GC genotype as the −28th nucleotide of the RANTES gene are shown for the SNPs of the MCC gene and SNPs of the RANTES gene. SPSS program version 10.0 was used for the contingency table analysis and calculation of the odds ratio, 95% confidence interval and P-value (significance value: P-value was calculated using $\chi^2$ test or Fisher's exact test).

(Results)

SNPs of 3255th nucleotide of the MCC gene and SNPs of −28th nucleotide of the RANTES gene were analyzed for AD patients and normal persons. The test subjects were classified into those having allele of the 3255th nucleotide the MCC gene of GG genotype and the others (allele of each gene of AG+AA genotype), and into those having allele of the −28th nucleotide the RANTES gene of CC genotype and the others (GG+CG), and AD morbidity rate was determined in each combination of respective classified groups to determine the odds ratio. The results showed that AD morbidity rate was high in the group (N=55) having GG genotype as SNPs of 3255th nucleotide of the MCC gene and having SNPs other than CC (GG or CG) genotype of −28th nucleotide of the RANTES gene. The odds ratio for the group (N=117) having SNPs other than GG (AG or AA) genotype of the MCC gene and SNPs of CC genotype of −28th nucleotide of the RANTES gene was 4.39 (p<0.001) as shown in Table 8.

Example 9

SNPs Analysis of MCC Gene and IL-13 Gene of AD Patient (Methods)

Peripheral blood lymphocytes were collected from 114 Japanese AD patients and 111 Japanese normal persons, and SNPs of the MCC gene and SNPs of IL-13 gene (4257th nucleotide) were analyzed by the PCR-RFLP methods as in the method described in Examples 1 and 5. The combination of homozygote and heterozygote, and the combination of the other heterozygote derived in Examples 1 and 5 were selected as the analysis condition, and the data were analyzed by comparing the data, in which the combination of homozygote and heterozygote is combined with the other homozygote respectively, between the AD patient and normal person. The result of analysis of a combination of a person having AA+AG genotype as the 3255th nucleotide of the MCC gene that shows the highest odds ratio and a person having GG genotype as the 4257th nucleotide of the IL-13 gene, and the result of analysis of a combination of a person having GG genotype as the 3255th nucleotide of the MCC gene and a person having AG+AA genotype as the 4257th nucleotide of the IL-13 gene are shown for the SNPs of the MCC gene and the IL-13 gene (4257th nucleotide). SPSS program version 10.0 was used for the contingency table analysis and calculation of the odds ratio, 95% confidence interval and P-value (significance value: P-value was calculated using $\chi^2$ test or Fisher's exact test).

(Results)

SNPs of 3255th nucleotide of the MCC gene and SNPs of 4257th nucleotide of the IL-13 gene were analyzed for AD patients and normal persons. The test subjects were classified into those having allele of the MCC gene of GG genotype and the other (allele of each gene of AA+AG) genotype, and into those having allele of the IL-13 gene of GG genotype and the other (allele of each gene of AG+AA) genotype, and AD morbidity rate was determined in each combination of respective classified groups to determine the odds ratio. The results showed that AD morbidity rate was high in the group (N=62) having GG genotype as SNPs of 3255th nucleotide of the MCC gene and having AG or AA genotype as SNPs 4257th nucleotide of the IL-13 gene. The odds ratio for the group (N=63) having SNPs other than GG (AA or AG) genotype of the MCC gene and SNPs of GG genotype of the IL-13 gene was 3.31 (p=0.001) as shown in Table 9.

TABLE 8

| MCC 3255 genotype | RANTES -28 genotype | n | Normal person | AD patient | Odds ratio (95% CI) | Significant difference |
|---|---|---|---|---|---|---|
| AA + AG | CC | 1172 | 50 (43%) | 67 (57%) | | |
| GG | GG + CG | 55 | 8 (15%) | 47 (85%) | 4.39 (1.90-10.10) | P < 0.001 |

TABLE 9

| MCC 3255 genotype | IL-13 4257 genotype | n | Normal person | AD patient | Odds ratio (95% CI) | Significant difference |
|---|---|---|---|---|---|---|
| AA + AG | GG | 63 | 35 (56%) | 28 (44%) | | |
| GG | AA + AG | 62 | 17 (27%) | 45 (73%) | 3.31 (1.57-6.99) | P < 0.001 |

The results in Examples 1 to 5 show that the morbidity risk of AD may be predicted to a certain extent by each analysis of the MCC gene alone (odds ratio=1.88. p<0.04), FCεRIβ gene alone (odds ratio=1.59, p<0.028), RANTES −403 gene alone (odds ratio=1.42, p<0.043), RANTES −28 gene alone (odds ratio=1.95, p<0.001) and IL-13 gene alone (odds ratio<1.79, p<0.004).

On the other hand, the morbidity risk of AD may be diagnosed in higher accuracy by analyzing SNPs of the MCC gene as well as by analyzing the combination of SNPs of the MCC gene and SNPs of the FcεRIβ gene, SNPs of RANTES gene (−403rd and 28th) or SNPs of the IL-13 gene as shown in Examples 6 to 9.

From the consideration that MCC is related to the symptom of AD, MCC inhibitor may be effective in the AD model, IgE is important in AD and an antagonist of IgE is effective in the allergy model, it is shown that administration of the MCC inhibitor, administration of anti-IgE antibody that suppresses the function of IgE and administration of a drug that suppresses the function of RANTES or IL-13 may be efficient in the patients having a combination of high morbidity risk of AD from the results of analysis of the combinations of SNPs of the MCC gene and SNPs of the FcεRIβ gene, RANTES gene or IL-1 gene (Table 10).

Further, AD patients called as non-allergic type or intrinsic type who do not exhibit elevation of the blood IgE level can be detected by using this diagnostic method. It is considered that an effective treatment for these patients can be determined by using this diagnostic method.

TABLE 10

| | FcεRIβ 1343 | RANTES -403 | RANTES -28 | IL-13 4257 |
|---|---|---|---|---|
| MCC 3255 | 4.82 P < 0.001 | 2.48 P < 0.003 | 4.39 P < 0.001 | 3.31 P < 0.001 |

Industrial Applicability

The method of the present invention enables prediction of relative risk rate for the morbidity of AD by measuring the genotype of blood component samples from patients, and may be used in the diagnosis of AD.

The invention claimed is:

1. A method of discriminating a relative risk for morbidity of atopic dermatitis of a test subject, comprising (i) a step of preparing a sample which contains a gene as an object of analysis and derives from a test subject and (ii) a step of determining individual gene polymorphism in combination with any two steps selected from steps (a) to (e) below:

(a) a step of analyzing gene polymorphism of human mast cell chymase gene extracted from the sample isolated from the test subject by determining which of guanine and adenine is the 3255th nucleotide of the nucleotide sequence represented by SEQ ID NO: 1;

(b) a step of analyzing gene polymorphism of human high affinity IgE receptor β-chain (FcεRIβ) gene extracted from the sample isolated from the test subject by determining which of guanine and adenine is the 1343rd nucleotide from the initiation codon of the nucleotide sequence represented by SEQ ID NO: 2;

(c) a step of analyzing gene polymorphism of RANTES gene extracted from the sample isolated from the test subject by determining which of guanine and adenine is the −403rd nucleotide at the upstream side counted from the transcription initiation site of mRNA of the nucleotide sequence represented by SEQ ID NO: 3;

(d) a step of analyzing gene polymorphism of RANTES gene extracted from the sample isolated from the test subject by determining which of guanine and cytosine is the −28th nucleotide at the upstream side counted from the transcription initiation site of mRNA of the nucleotide sequence represented by SEQ ID NO: 3; and (e) a step of analyzing gene polymorphism of interleukin-13 gene extracted from the sample isolated from the test subject by determining which of guanine and adenine is the 4257th nucleotide of the nucleotide sequence represented by SEQ ID NO: 4.

2. The method according to claim 1, wherein the two steps are a combination of steps (a) and (b), steps (a) and (c), steps (a) and (d), or steps (a) and (e).

3. The method according to claim 1 wherein the two steps are (a) and (b), (a) and (d) or (a) and (e).

4. The method according to claim 1 wherein the two steps are steps (a) and (b), or steps (a) and (d).

5. The method according to claim 1 wherein the two steps are steps (a) and (b).

6. The method according to claim 1, wherein the sample is prepared from blood, skin cells, mucous membrane cells, hair or urine of the test subject.

7. A method of discriminating a relative risk for morbidity of atopic dermatitis of a test subject, comprising (i) a step of preparing a sample which contains a gene as an object of analysis and derives from a test subject and (ii) a step of determining individual gene polymorphism in combination with any two steps selected from the steps of (g) to (k) below;

(g) a step of analyzing gene polymorphism of human mast cell chymase gene extracted from the sample isolated from the test subject by determining which of guanine-guanine homozygote, guanine-adenine heterozygote and adenine-adenine homozygote is the combination of the 3255th nucleotide of the nucleotide sequence represented by SEQ ID NO: 1;

(h) a step of analyzing gene polymorphism of human high affinity IgE receptor β-chain (FcεRIβ) gene extracted from the sample isolated from the test subject by determining which of guanine-guanine homozygote, guanine-adenine heterozygote and adenine-adenine homozygote is the combination of the 1343rd nucleotide from the initiation codon of the nucleotide sequence represented by SEQ ID NO: 2;

(i) a step of analyzing gene polymorphism of RANTES gene extracted from the sample isolated from the test subject by determining which of guanine-guanine homozygote, guanine-adenine heterozygote and adenine-adenine homozygote is the combination of the −403rd nucleotide at the upstream side counted from the transcription initiation site of the mRNA of the nucleotide sequence represented by SEQ ID NO: 3;

(j) a step of analyzing gene polymorphism of RANTES gene extracted from the sample isolated from the test subject by determining which of guanine-guanine homozygote, guanine-cytosine heterozygote and cytosine-cytosine homozygote is the combination of the −28th nucleotide at the upstream side counted from the transcription initiation site of mRNA of the nucleotide sequence represented by SEQ ID NO: 3; and (k) a step of analyzing gene polymorphism of interleukin-13 gene extracted from the sample isolated from the test subject determining which of guanine-guanine homozygote, guanine-adenine heterozygote and adenine-adenine homozygote is the combination of the 4257th nucleotide of the nucleotide sequence represented by SEQ ID NO: 4.

8. The method according to claim 7, wherein the two steps are a combination of steps (g) and (h), steps (g) and (i), steps (g) and (j) or steps (g) and (k).

9. The method according to claim 7, wherein the sample is prepared from blood, skin cells, mucous membrane cells, hair or urine of the test subject.

* * * * *